US010399949B2

(12) United States Patent
Miyagi et al.

(10) Patent No.: US 10,399,949 B2
(45) Date of Patent: Sep. 3, 2019

(54) NK1 RECEPTOR ANTAGONIST

(71) Applicant: KISSEI PHARMACEUTICAL CO., LTD., Matsumoto-shi, Nagano (JP)

(72) Inventors: Takashi Miyagi, Azumino (JP); Masahiro Kobayashi, Matsumoto (JP); Toshihiro Nishimura, Azumino (JP)

(73) Assignee: KISSEI PHARMACEUTICAL CO., LTD., Matsumoto-shi, Nagano (JP)

( * ) Notice: Subject to any disclaimer, the term of this patent is extended or adjusted under 35 U.S.C. 154(b) by 0 days.

(21) Appl. No.: 15/781,925

(22) PCT Filed: Dec. 6, 2016

(86) PCT No.: PCT/JP2016/086150
§ 371 (c)(1),
(2) Date: Jun. 6, 2018

(87) PCT Pub. No.: WO2017/099049
PCT Pub. Date: Jun. 15, 2017

(65) Prior Publication Data
US 2019/0002414 A1    Jan. 3, 2019

(30) Foreign Application Priority Data

Dec. 7, 2015  (JP) .................. 2015-238122

(51) Int. Cl.
*C07D 211/62*      (2006.01)
*C07D 241/04*      (2006.01)
*C07D 401/06*      (2006.01)
*A61K 31/495*      (2006.01)
*A61K 31/496*      (2006.01)
*A61K 31/451*      (2006.01)
*A61P 1/08*        (2006.01)
*C07D 211/32*      (2006.01)

(52) U.S. Cl.
CPC .......... *C07D 241/04* (2013.01); *A61K 31/451* (2013.01); *A61K 31/495* (2013.01); *A61P 1/08* (2018.01); *C07D 211/32* (2013.01); *C07D 211/62* (2013.01); *C07D 401/06* (2013.01)

(58) Field of Classification Search
CPC ... C07D 211/62; C07D 241/04; C07D 401/06
See application file for complete search history.

(56) References Cited

U.S. PATENT DOCUMENTS

| 9,708,266 | B2 | 7/2017 | Shimizu et al. |
| 2002/0091265 | A1 | 7/2002 | Bos et al. |
| 2004/0048862 | A1 | 3/2004 | Alvaro et al. |
| 2005/0239829 | A1 | 10/2005 | Takahashi et al. |
| 2008/0275085 | A1 | 11/2008 | Shirai et al. |
| 2009/0005355 | A1 | 1/2009 | Miyake et al. |
| 2016/0289206 | A1 | 10/2016 | Shimizu et al. |

FOREIGN PATENT DOCUMENTS

| JP | 2003-511377 A | 3/2003 |
| JP | 2004-143139 A | 5/2004 |
| JP | 2006-45208 A  | 2/2006 |
| JP | 2007-197428 A | 8/2007 |
| WO | 2008/133344 A2 | 11/2008 |
| WO | 2010/007032 A1 | 1/2010 |
| WO | 2015/068744 A1 | 5/2015 |
| WO | 2015/170693 A1 | 11/2015 |
| WO | 2016/021562 A1 | 2/2016 |

OTHER PUBLICATIONS

Pellegatti, Mario et al., "Disposition and Metabolism of Radiolabeled Casopitant in Humans", Drug Metabolism and Disposition, vol. 37, No. 8, 2009, pp. 1635-1645 (in English, cited in the ISR).
International Search Report dated Feb. 28, 2017, issued in counterpart International patent application No. PCT/JP2016/086150 (w/ English translation; 8 pages).

*Primary Examiner* — Emily A Bernhardt
(74) *Attorney, Agent, or Firm* — Westerman, Hattori, Daniels & Adrian, LLP

(57) ABSTRACT

A problem of the present invention is to provide a new compound which has NK$_1$ receptor antagonist activity, and thus is useful for the prevention or treatment of cancer-chemotherapy-induced nausea and vomiting.
A compound represented by the formula (I):

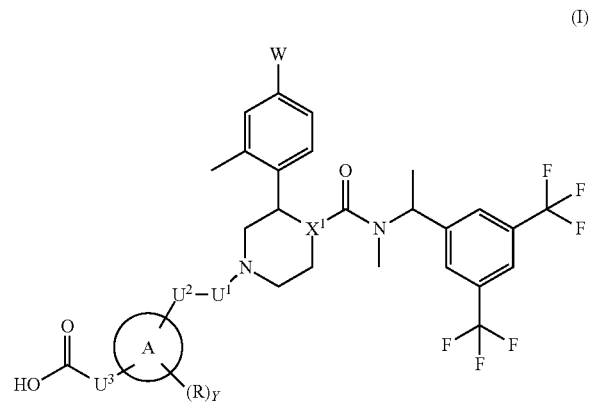

wherein W represents a fluorine atom and the like, ring A represents a cycloalkyl and the like, $X^1$ represents CH or N, R represents methyl and the like, Y represents 0 to 2, $U^1$, $U^2$ and $U^3$ each independently represents a single bond and the like, or a pharmaceutically acceptable salt thereof. The compounds of the present invention or pharmaceutically acceptable salts thereof have an excellent NK$_1$ receptor antagonist activity, and thus are also useful as an agent for the prevention or treatment of cancer-chemotherapy-induced nausea and vomiting.

11 Claims, No Drawings
Specification includes a Sequence Listing.

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: forward primer

<400> SEQUENCE: 1
tacctcgaga gatagtaggg ctttaccg                                       28

<210> SEQ ID NO 2
<211> LENGTH: 28
<212> TYPE: DNA
<213> ORGANISM: Artificial Sequence
<220> FEATURE:
<223> OTHER INFORMATION: reverse primer

<400> SEQUENCE: 2
gccaagcttc taggagagca cattggag                                       28

<210> SEQ ID NO 3
<211> LENGTH: 1224
<212> TYPE: DNA
<213> ORGANISM: Homo sapiens

<400> SEQUENCE: 3
atggataacg tcctcccggt ggactcagac ctctccccaa acatctccac taacacctcg    60
gaacccaatc agttcgtgca accagcctgg caaattgtcc tttgggcagc tgcctacacg   120
gtcattgtgg tgacctctgt ggtgggcaac gtggtagtga tgtggatcat cttagcccac   180
aaaagaatga ggacagtgac gaactatttt ctggtgaacc tggccttcgc ggaggcctcc   240
atggctgcat tcaatacagt ggtgaacttc acctatgctg tccacaacga atggtactac   300
ggcctgttct actgcaagtt ccacaacttc tttcccatcg ccgctgtctt cgccagtatc   360
tactccatga cggctgtggc cttttgatagg tacatggcca tcatacatcc cctccagccc   420
cggctgtcag ccacagccac caaagtggtc atctgtgtca tctgggtcct ggctctcctg   480
ctggccttcc ccagggcta ctactcaacc acagagacca tgcccagcag agtcgtgtgc   540
atgatcgaat ggcagagca tccgaacaag atttatgaga aagtgtacca catctgtgtg   600
actgtgctga tctacttcct cccccctgctg gtgattggct atgcatacac cgtagtggga   660
atcacactat gggccagtga gatccccggg gactcctctg accgctacca cgagcaagtc   720
tctgccaagc gcaaggtggt caaaatgatg attgtcgtgg tgtgcacctt cgccatctgc   780
tggctgccct tccacatctt cttcctcctg ccctacatca acccagatct ctacctgaag   840
aagtttatcc agcaggtcta cctggccatc atgtggctgg ccatgagctc caccatgtac   900
aaccccatca tctactgctg cctcaatgac aggttccgtc tgggcttcaa gcatgccttc   960
cggtgctgcc ccttcatcag cgccggcgac tatgagggc tggaaatgaa atccacccgg  1020
tatctccaga cccagggcag tgtgtacaaa gtcagccgcc tggagaccac catctccaca  1080 gtggtgggg cccacgagga ggagccagag gacggcccca aggccacacc ctcgtccctg  1140
gacctgacct ccaactgctc ttcacgaagt gactccaaga ccatgacaga gagcttcagc  1200
ttctcctcca atgtgctctc ctag                                        1224

NK1 RECEPTOR ANTAGONIST

TECHNICAL FIELD

The present invention relates to $NK_1$ receptor antagonist useful as medicaments.

More particularly, the present invention relates to $NK_1$ receptor antagonist or pharmaceutically acceptable salts thereof which have substance P/neurokinin 1 ($NK_1$) receptor antagonist activity, and which are useful as agents for the prevention or treatment of cancer-chemotherapy-induced nausea and vomiting (CINV) and so on.

BACKGROUND ART

CINV occurs when the vomiting center located in the lateral reticular formation of the medulla oblongata receives a stimulus. The area postrema and the solitary nucleus of the medulla oblongata contain $NK_1$ receptors, and the $NK_1$ receptors are believed to be closely involved in vomiting.

Administration of an antineoplastic agent facilitates the serotonin secretion from the enterochromaffin (EC) cells in the digestive tract, and serotonin directly stimulates the vomiting center through 5-hydroxytryptamine$_3$ (5-HT$_3$) receptors in the digestive tract. Also, when serotonin stimulates the vomiting center through the chemoreceptor trigger zone (CTZ) located in the area postrema of the fourth ventricle, nausea and vomiting occur. Substance P, like serotonin, is found in the EC cells in the digestive tract, and its secretion is promoted by administration of an antineoplastic agent. Recently, it has been revealed that substance P induces vomiting through the $NK_1$ receptors in the CTZ or by binding to the $NK_1$ receptors in the central nervous system, and therefore $NK_1$ receptors have been attracting attention as the target for developing antiemetic agents (Non-patent literature 1).

Aprepitant is the first selective $NK_1$ receptor antagonist in the world which was approved as a preventive agent for nausea and vomiting associated with administration of antineoplastic agents. Regarding the mechanism of action of aprepitant, it is believed that aprepitant selectively inhibits the binding of substance P and the $NK_1$ receptors in the central nervous system, which is one of the pathways that induce CINV, and thus prevents CINV. Aprepitant has been launched as a preventive agent for CINV (Non-patent literature 2).

It is known that aprepitant is metabolized by cytochrome P450 (CYP) 3A4. Also, aprepitant is known to have a dose-dependent inhibitory effect on CYP3A4, a CYP3A4-inducing effect and a CYP2C9-inducing effect. Accordingly, aprepitant may cause the drug-drug interactions with drugs that inhibit or induce CYP3A4 or with drugs that are metabolized by CYP3A4 or CYP2C9. For example, it is reported that the inhibitory effect of aprepitant on CYP3A4 sometimes inhibits the metabolism of dexamethasone and that the dose should be thus adjusted when dexamethasone is combined with aprepitant (Non-patent literature 3).

Therefore, when aprepitant is used, sufficient care should be directed to the drug-drug interactions based on the inhibitory effect of aprepitant on CYP3A4, a novel $NK_1$ receptor antagonist is required as a preventive agent for CINV.

Compounds with an $NK_1$ receptor antagonist activity are described in Patent literature 1 to 4.

However, in the above literatures, anything is neither described nor suggested about the $NK_1$ receptor antagonist of the present invention.

CITATION LIST

Patent Literature

Patent literature 1: Japanese patent publication No. 2003-511377 gazette.

Patent literature 2: Japanese patent publication No. 2006-45208 gazette.

Patent literature 3: Japanese patent publication No. 2007-197428 gazette.

Patent Literature 4: International Publication WO 2008/133344

Non-Patent Literature

Non-patent literature 1: P. J. Hesketh et al., European Journal of Cancer, 2003, Vol. 39, pp. 1074-1080

Non-patent literature 2: Toni M. Dando et al., Drugs, 2004, Vol. 64, No. 7, pp. 777-794

Non-patent literature 3: Jacqueline B. McCrea et al., CLINICAL PHARMACOLOGY & THERAPEUTICS, 2003, Vol. 74, No. 1, pp. 17-24

SUMMARY OF THE INVENTION

Problems to be Solved by the Invention

A problem of the present invention is to provide a new compound which has $NK_1$ receptor antagonist activity and which are useful for the prevention or treatment of cancer-chemotherapy-induced nausea and vomiting.

Means for Solving the Problems

The present invention relates to a compound represented by the following formula (I) or a pharmaceutically acceptable salt thereof.

That is, the present invention relates to the following [1] to [10] and the like.

[1] A compound represented by the formula (I):

[Chem. 1]

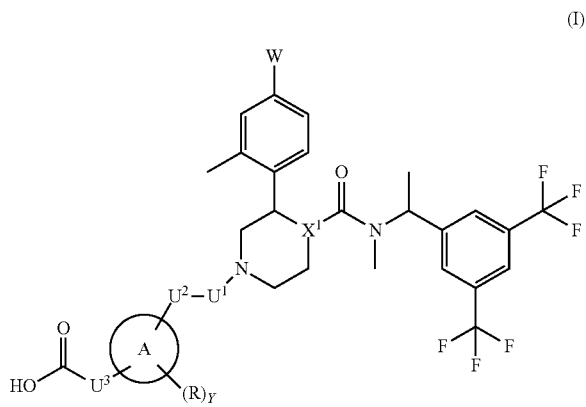

(I)

wherein
W is a hydrogen atom or a fluorine atom;
ring A is a group selected from the group consisting of the following (a) to (d):

[Chem. 2]

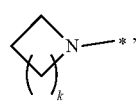

(a)

-continued (b)

<chemical structure>

(c)

<chemical structure>
and (d)

<chemical structure> wherein
bonds with * are bonding site to the $U^2$;
k represents an integer number 1 to 5;
r is 1 or 2;
m and n are each independently 1, 2 or 3;
$X^1$ is CH or N;
R is a methyl, hydroxy or a halogen atom;
Y is 0, 1 or 2;
when Y is 2, two R are optionally different from each other;
$U^1$, $U^2$ and $U^3$ are each independently a single bond, carbonyl or a methylene which may have any group selected from substituent group α;
when ring A is a group represented by the above (a), either one of $U^1$ or $U^2$ is carbonyl; substituent group α is a group consisting of a halogen atom, hydroxy, a $C_{1-6}$ alkyl and a $C_{1-6}$ alkoxy;
or a pharmaceutically acceptable salt thereof.

[2] The compound according to the above [1] or a pharmaceutically acceptable salt thereof, wherein $X^1$ is N.

[3] The compound according to [1] or [2] or a pharmaceutically acceptable salt thereof, wherein W is a fluorine atom.

[4] The compound represented by the formula (Ia) according to the above [3]:

[Chem. 3]

<chemical structure> (Ia)

wherein
ring B is a group represented by the following formula:

[Chem. 4]

<chemical structure>, or <chemical structure>;

wherein
bonds with * are bonding site to the $U^2$;
$U^1$, $U^2$ and $U^3$ have the same meaning as described in the above [1];
or a pharmaceutically acceptable salt thereof.

[5] The compound represented by the formula (Ib) according to the above [4]:

[Chem. 5]

<chemical structure> (Ib)

wherein
$U^4$, $U^5$ and $U^6$ are each independently a single bond or a methylene which may have any substituent selected from substituent group α;
substituent group α has the same meaning as described in the above [1];
or a pharmaceutically acceptable salt thereof.

[6] The compound represented by the formula (Ic) according to the above [5]:

[Chem. 6]

<chemical structure> (Ic)

wherein
$U^7$ and $U^8$ are each independently a single bond or a methylene which may have any substituent selected from substituent group β;
substituent group β is a group consisting of a fluorine atom and methyl;
or a pharmaceutically acceptable salt thereof.

[7] The compound represented by the formula (Id) according to the above [6]:

[Chem. 7]

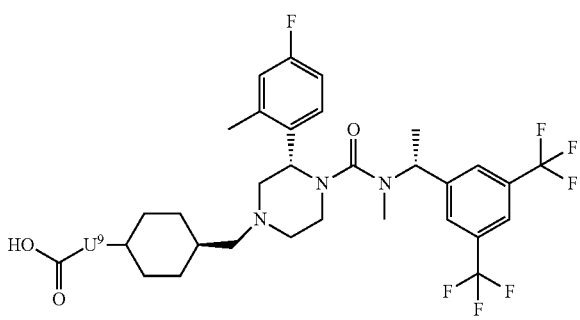

(Id)

wherein
U⁹ is a single bond or a methylene;
or a pharmaceutically acceptable salt thereof.
[8] The compound represented by the formula (Ie) according to the above [1]:

[Chem. 8]

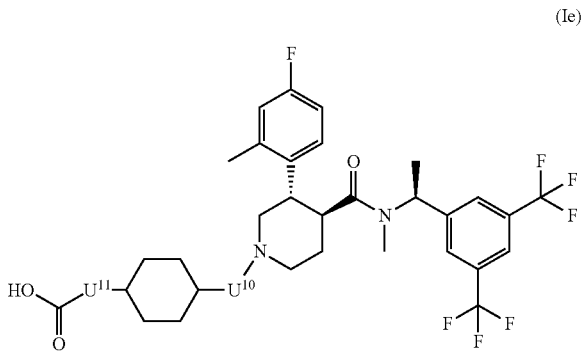

(Ie)

wherein
$U^{10}$ and $U^{11}$ are each independently a single bond or a methylene;
or a pharmaceutically acceptable salt thereof.
[9] A pharmaceutical composition comprising the compound according to any one of the above [1] to [8] or a pharmaceutically acceptable salt thereof.
[10] The pharmaceutical composition according to the above [9], for use in the prevention of cancer-chemotherapy-induced nausea and vomiting.

Effect of the Invention

The compounds of the present invention have an excellent $NK_1$ receptor antagonist activity. Therefore, the compounds of the present invention or pharmaceutically acceptable salts thereof are useful as an agent for the prevention or treatment of cancer-chemotherapy-induced nausea and vomiting.

BRIEF DESCRIPTION OF THE DRAWINGS

Hereinafter, embodiments of the present invention will be described in further detail.
In the present invention, each term has the following meaning unless otherwise specified.

The term "$C_{1-6}$ alkyl" means a straight-chained or a branched alkyl group having 1 to 6 carbon atoms, and for example, methyl, ethyl, propyl, isopropyl, butyl, isobutyl, sec-butyl, tert-butyl and the like can be illustrated.

The term "$C_{1-6}$ alkoxy" means a straight-chained or a branched alkoxy group having 1 to 6 carbon atoms, and for example, methoxy, ethoxy, propoxy, isopropoxy and the like can be illustrated.

The term "methylene which may have any group selected from substituent group α" means optionally having 1 to 2 same or different groups selected from substituent group α, and having none or 1 substituent is preferred.

The term "methylene which may have any group selected from substituent group β" means optionally having 1 to 2 same or different groups selected from substituent group β, and having none or 1 substituent is preferred.

In the case where the compounds represented by the formula (I) of the present invention contain one or more asymmetric carbon atoms, all stereoisomers in the R- or S-configuration at each of asymmetric carbons and their mixtures are included in the present invention. In such cases, racemic compounds, racemic mixtures, individual enantiomers and mixtures of diastereomers are included in the scope of the present invention. In the case where the compounds represented by the formula (I) of the present invention have the cis-trans isomers, all cis-trans isomers are included in the present invention.

In the present invention, stereochemical structures can also be determined according to well-known methods in the art. For example, see also "Tokuron NMR rittai kagaku", Kodansha, 2012, p. 59.

A compound represented by the formula (I) of the present invention can be converted into pharmaceutically acceptable salts thereof according to a conventional method. As such salts, acid addition salts and salts with a base can be illustrated.

As the acid addition salt, an acid addition salt formed with mineral acids such as hydrochloric acid, hydrobromic acid, hydroiodic acid, sulfuric acid, nitric acid, phosphoric acid and the like, and an acid addition salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid, aspartic acid and the like can be illustrated.

As the salt with a base, a salt formed with inorganic base such as a lithium, a sodium, a potassium, a calcium, a magnesium and the like, and a salt formed with organic base such as N-methyl-D-glucamine, N,N'-dibenzylethylenediamine, triethylamine, piperidine, morpholine, pyrrolidine, arginine, lysine, choline and the like.

In the present invention, a pharmaceutically acceptable salt also includes a solvate thereof with a pharmaceutically acceptable solvent such as water, ethanol or the like.

A compound represented by the formula (I) of the present invention can also be prepared, for example, by a method described below or a similar method thereto, or a method described in literatures or a similar method thereto.

In an embodiment of a compound represented by the formula (I) of the present invention, ring A may be used 5 or 6-membered heteroaryl such as thiazolyl, pyrrolyl, imidazolyl, thienyl, furyl, pyridyl and the like; 3 to 8-membered heterocycloalkyl such as piperazinyl, tetrahydrofuryl, morpholinyl and the like; heterocyclic compounds such as indolyl, benzimidazolyl, imidazopyrazinyl, imidazopyridinyl and the like.

In an embodiment of a compound represented by the formula (I) of the present invention, Y is preferably 0.

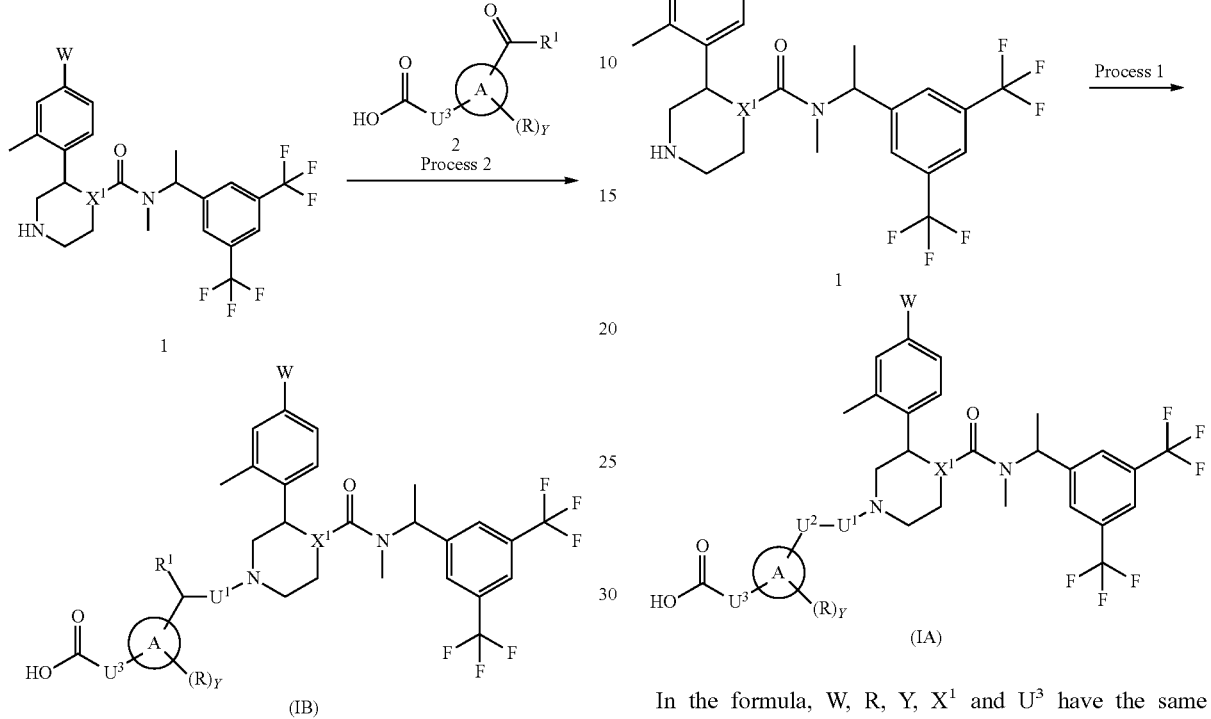

In an embodiment of a compound represented by the formula (I) of the present invention, $U^1$ and $U^2$ are preferably a group selected from the group consisting of the following (1) to (6):

(1) $U^1$ is a single bond and $U^2$ is a single bond;
(2) $U^1$ is a single bond and $U^2$ is a methylene which may have any group selected from substituent group α;
(3) $U^1$ is a single bond and $U^2$ is a carbonyl;
(4) $U^1$ is a methylene which may have any group selected from substituent group α and $U^2$ is a carbonyl;
(5) $U^1$ is a carbonyl and $U^2$ is a methylene which may have any group selected from substituent group α; and
(6) $U^1$ is a methylene which may have any group selected from substituent group α and $U^2$ is a methylene which may have any group selected from substituent group α.

A compound represented by the formula (I) of the present invention can also be prepared as a compound (IA) to (IK), for example, by a method described in Scheme 1 to Scheme 11 or a similar method thereto, or a method described in literatures or a similar method thereto.

A compound represented by the formula (IA) can be prepared, for example, by a method described in Process 1 of Scheme 1.

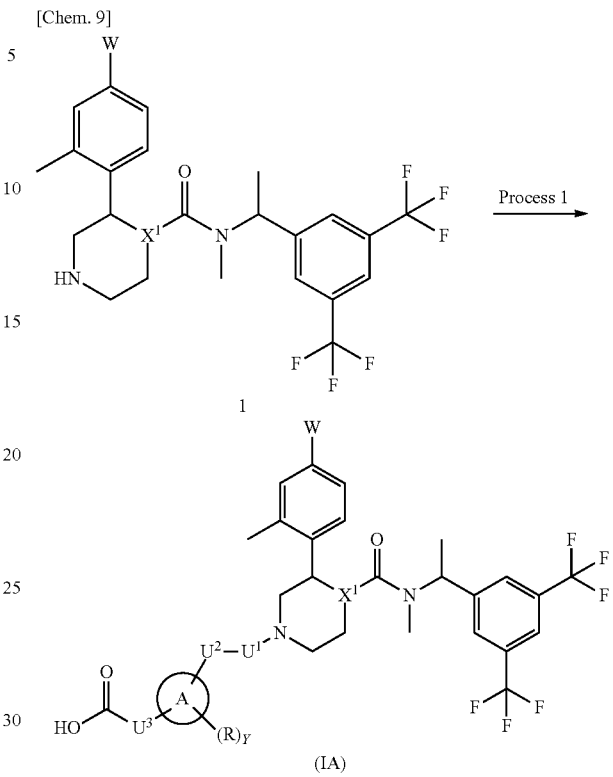

In the formula, W, R, Y, $X^1$ and $U^3$ have the same meanings as defined above. Ring A is a group as described in above (b). $U^1$ is a single bond and $U^2$ is a single bond.

Process 1

Compound (IA) can also be prepared by reacting Compound (1) with a cyclic ketone compound in an inert solvent and then reacting with a reductant in the presence or absence of acetic acid. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the reductant, sodium borohydride, sodium cyanoborohydride, sodium triacetoxyborohydride, 2-picoline borane or the like can be illustrated. The reaction temperature is usually at 0° C. to reflux temperature. The reaction time is usually from 10 minutes to 7 days, varying based on a used starting material, solvent and reaction temperature or the like. As compounds synthesized by Process 1, for example, Example 1, 6, 12 and the like can be illustrated.

A compound represented by the formula (TB) can be prepared, for example, by a method described in Process 2 of Scheme 2.

In the formula, W, R, Y, $X^1$ and $U^3$ have the same meanings as defined above. Ring A is a group selected from the group consisting of above (b), (c) and (d). $U^1$ is a single bond and $R^1$ is a hydrogen atom or a $C_{1-6}$ alkyl group.

Process 2

Compound (TB) can also be prepared by reacting Compound (1) with Compound (2) in an inert solvent and then reacting with a reductant in the presence or absence of acetic acid. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the reductant, sodium borohydride, sodium cyanoborohydride, sodium triacetoxyborohydride, 2-picoline borane or the like can be illustrated. The reaction temperature is usually at 0° C. to reflux temperature. The reaction time is usually from 10 minutes to 7 days, varying based on a used starting material, solvent and reaction temperature or the like. As compounds synthesized by Process 2, for example, Example 4, 5, 7, 8, 11, 13, 14 and the like can be illustrated.

A compound represented by the formula (IC) can be prepared, for example, by a method described in Process 3 of Scheme 3.

Scheme 3

[Chem. 11]

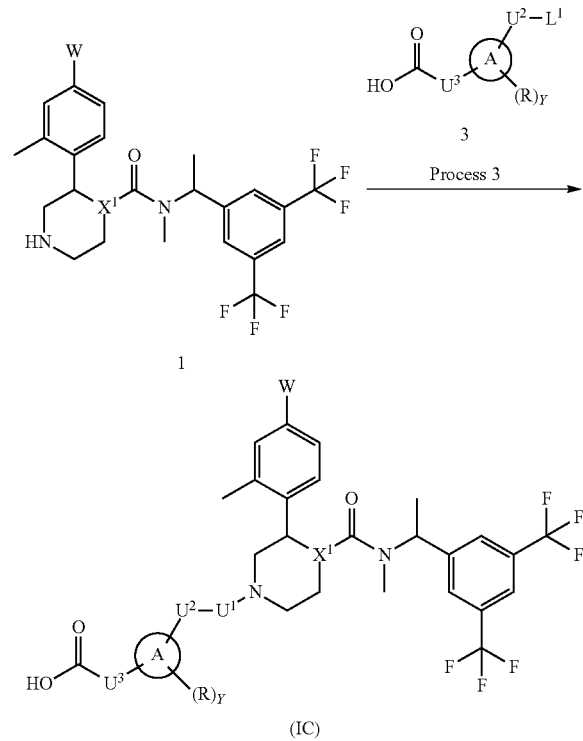

(IC)

In the formula, W, R, Y, $X^1$ and $U^3$ have the same meanings as defined above. Ring A is a group selected from the group consisting of above (b), (c) and (d). $U^1$ is a single bond and $U^2$ is a methylene which may have any substituent selected from substituent group α. $L^1$ represents a leaving group such as a chlorine atom, a bromine atom, an iodine atom and the like.

Process 3

Compound (IC) can also be prepared by reacting Compound (1) with Compound (3) in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. The reaction temperature is usually at 0° C. to reflux temperature. The reaction time is usually from 30 minutes to 7 days, varying based on a used starting material, solvent and reaction temperature or the like. As compounds synthesized by Process 3, for example, Example 9 and the like can be illustrated.

A compound represented by the formula (ID) can be prepared, for example, by a method described in Process 4A or 4B of Scheme 4.

Scheme 4

[Chem. 12]

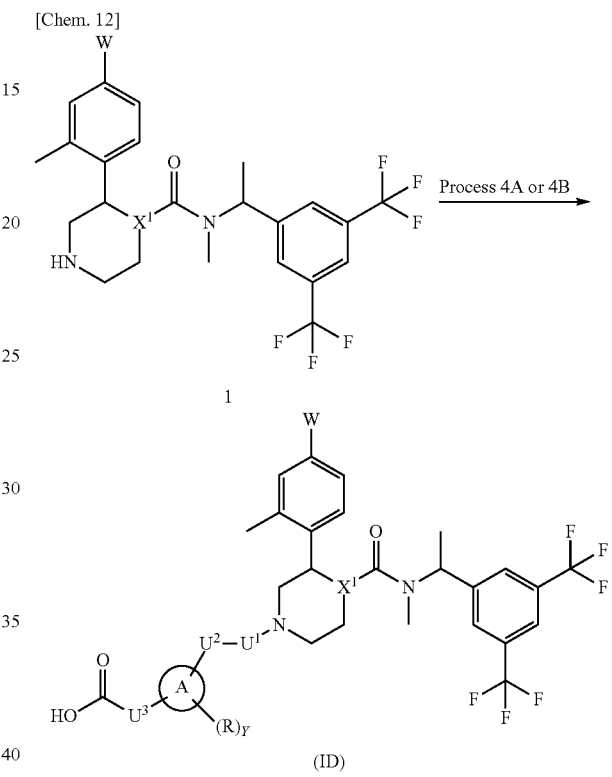

(ID)

In the formula, W, R, Y, $X^1$ and $U^3$ have the same meanings as defined above. Ring A is a group selected from the group consisting of above (b), (c) and (d). $U^1$ is a single bond and $U^2$ is a carbonyl.

Process 4A

Compound (ID) can also be prepared by conducting condensation reaction of Compound (1) with a carboxylic acid compound using condensation reagent in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. As the condensation reagent, 1,1'-carbonyldiimidazole (CDI), 1-hydroxybenzotriazole (HOBt), N,N'-dicyclohexylcarbodiimide (DCC), 1-(3-dimethylaminopropyl)-3-ethylcarbodiimide hydrochloride (Water Soluble Carbodiimide hydrochloride (WSCD.HCl)), PyBOP®, PyBroP®, O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) and the like can be illustrated. The reaction temperature is usually at 0° C. to reflux temperature. The reaction time is usually from 30 minutes to 7 days, varying based on a used starting material, solvent and reaction temperature or the like. As compounds synthesized by Process 4A, for example, Example 2, 3 and the like can be illustrated.

Process 4B

Compound (ID) can also be prepared by reacting Compound (1) with an acid chloride compound in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. The reaction temperature is usually at 0° C. to reflux temperature. The reaction time is usually from 10 minutes to 7 days, varying based on a used starting material, solvent and reaction temperature or the like.

A compound represented by the formula (IE) can be prepared, for example, by a method described in Process 5 of Scheme 5.

In the formula, W, R, Y, $X^1$ and $U^3$ have the same meanings as defined above. Ring A is a group selected from the group consisting of above (a), (b), (c) and (d). $U^1$ is a single bond and $U^2$ is a carbonyl.

Process 5

Compound (IE) can also be prepared by reacting Compound (1) with an active ester compound such as Compound (4) in an inert solvent in the presence or absence of a base. As the inert solvent, N,N-dimethylformamide, N-methylpyrrolidone, dimethyl-sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene can be illustrated. The reaction temperature is usually at 0° C. to reflux temperature. The reaction time is usually from 30 minutes to 7 days, varying based on a used starting material, solvent and reaction temperature or the like. As compounds synthesized by Process 5, for example, Example 10 and the like can be illustrated.

Scheme 5

[Chem. 13]

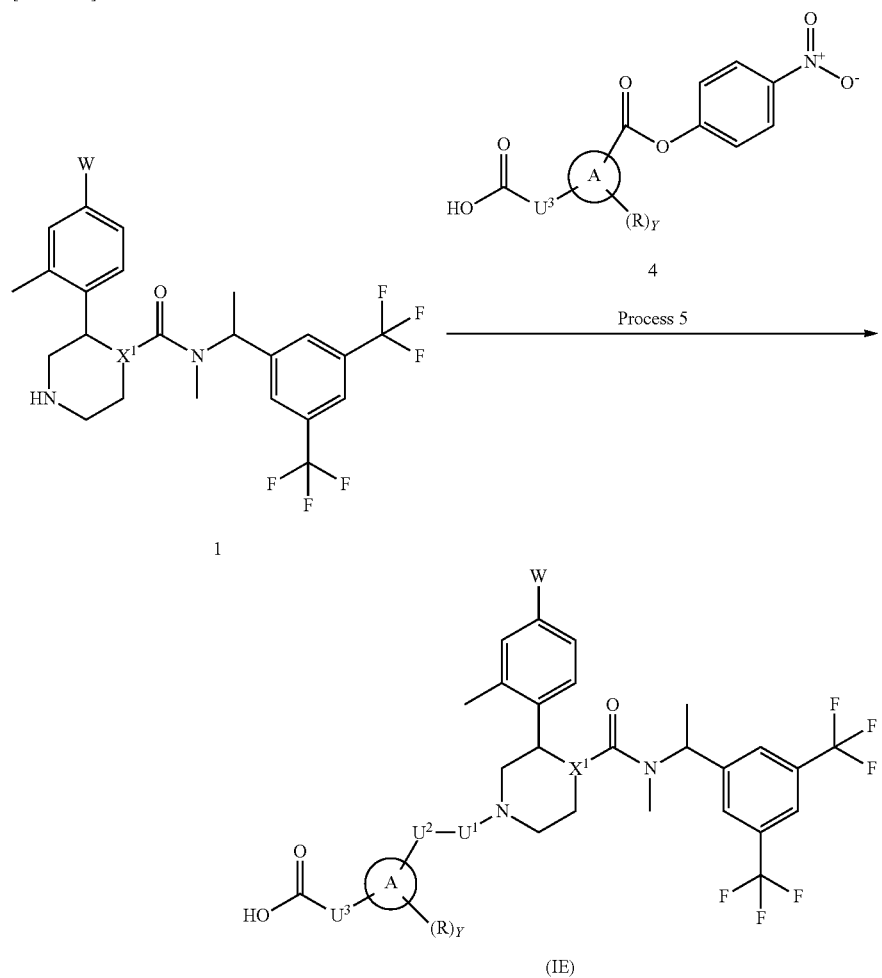

A compound represented by the formula (IF) can be prepared, for example, by a method described in Process 6 of Scheme 6.

Scheme 6

[Chem. 14]

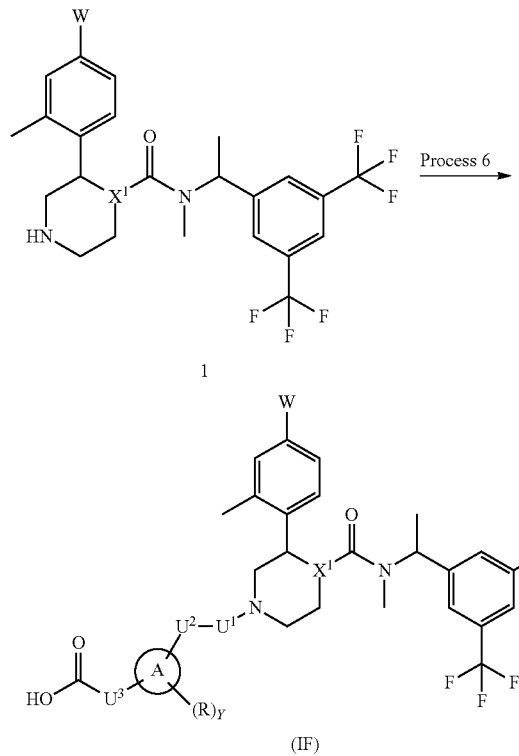

(IF)

In the formula, W, R, Y, $X^1$ and $U^3$ have the same meanings as defined above. Ring A is a group described above (a). $U^1$ is a single bond and $U^2$ is a carbonyl.

Process 6

Compound (IF) can also be prepared by reacting Compound (1) with a cyclic carboxylic acid compound by using a condensation reagent in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo [5.4.0]-7-undecene and the like can be illustrated. As the condensation reagent, CDI, triphosgene and the like can be illustrated. The reaction temperature is usually at 0° C. to reflux temperature. The reaction time is usually from 30 minutes to 7 days, varying based on a used starting material, solvent and reaction temperature or the like.

A compound represented by the formula (IG) can be prepared, for example, by a method described in Process 7 of Scheme 7.

Scheme 7

[Chem. 15]

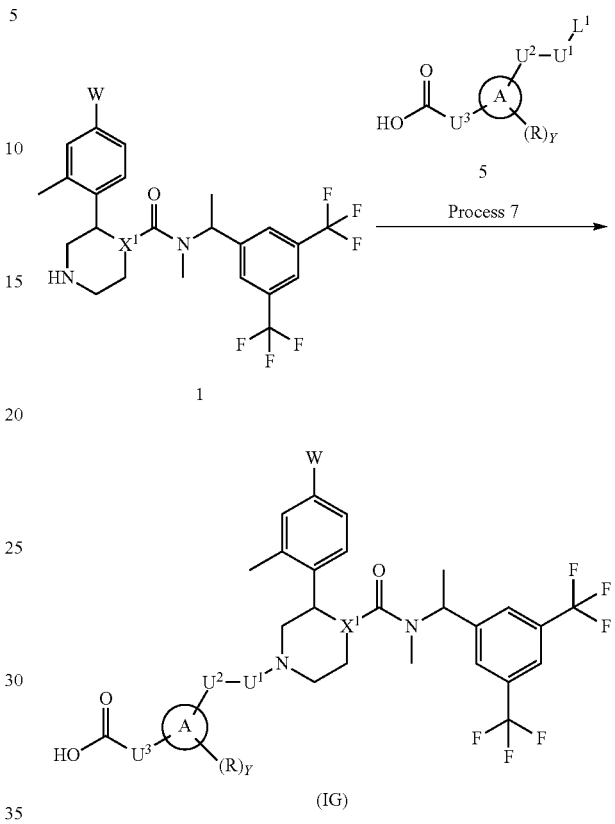

(IG)

In the formula, W, R, Y, $X^1$ and $U^3$ have the same meanings as defined above. Ring A is a group selected from the group consisting of above (a), (b), (c) and (d). $U^1$ is a methylene which may have any substituent selected from substituent group α and $U^2$ is a carbonyl. $L^1$ represents a leaving group such as a chlorine atom, a bromine atom, an iodine atom and the like.

Process 7

Compound (IG) can also be prepared by reacting Compound (1) with Compound (5) in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. The reaction temperature is usually at 0° C. to reflux temperature. The reaction time is usually from 30 minutes to 7 days, varying based on a used starting material, solvent and reaction temperature or the like.

A compound represented by the formula (IH) can be prepared, for example, by a method described in Process 8A or 8B of Scheme 8.

Scheme 8

[Chem. 16]

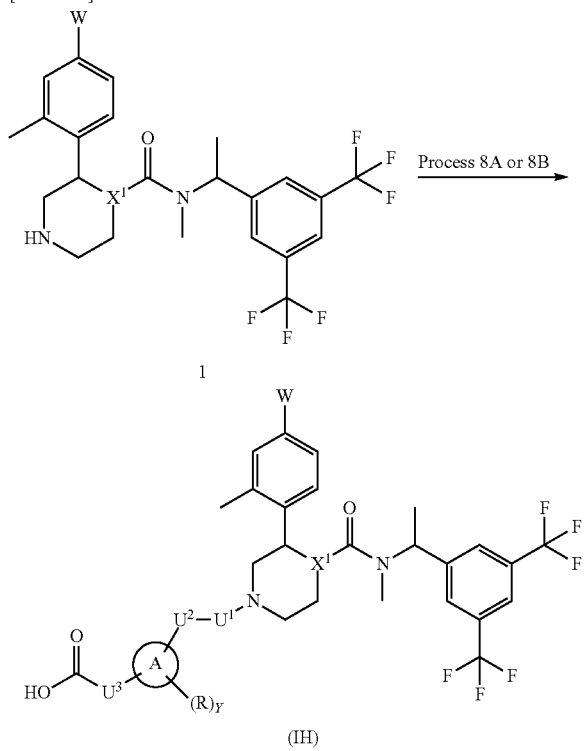

In the formula, W, R, Y, $X^1$ and $U^3$ have the same meanings as defined above. Ring A is a group selected from the group consisting of above (a), (b), (c) and (d). $U^1$ is a carbonyl and $U^2$ is a methylene which may have any substituent selected from substituent group α.

Process 8A

Compound (IH) can also be prepared by conducting condensation reaction of Compound (1) with a carboxylic acid compound by using a condensation reagent in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, for potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. As the condensation reagent, CDI, HOBt, DCC, WSCD.HCl, PyBOP®, PyBroP®, HATU, HBTU and the like can be illustrated. The reaction temperature is usually at 0° C. to reflux temperature. The reaction time is usually from 30 minutes to 7 days, varying based on a used starting material, solvent and reaction temperature or the like.

Process 8B

Compound (IH) can also be prepared by reacting Compound (1) with an acid chloride compound in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. The reaction temperature is usually at 0° C. to reflux temperature. The reaction time is usually from 10 minutes to 7 days, varying based on a used starting material, solvent and reaction temperature or the like.

A compound represented by the formula (IJ) can be prepared, for example, by a method described in Process 9 of Scheme 9.

Scheme 9

[Chem. 17]

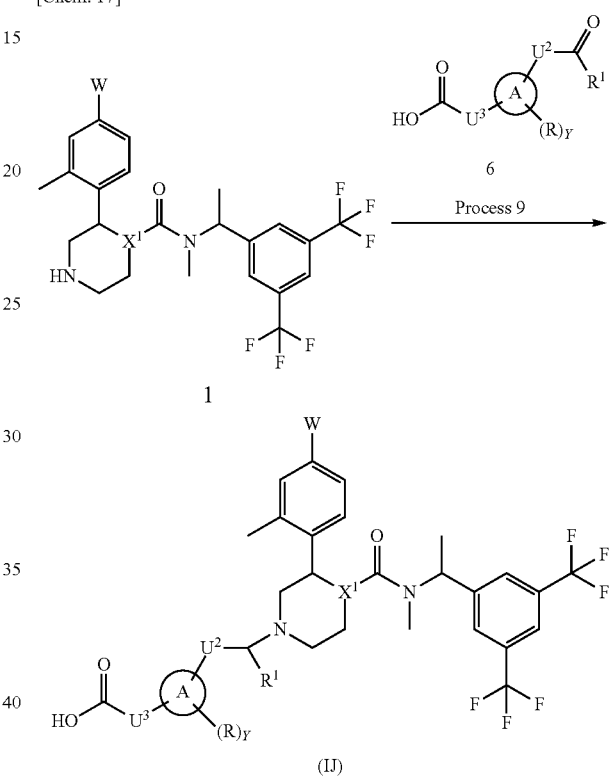

In the formula, W, R, Y, $X^1$ and $U^3$ have the same meanings as defined above. Ring A is a group selected from the group consisting of above (a), (b), (c) and (d). $U^2$ is a methylene which may have any substituent selected from substituent group α. $R^1$ represents a hydrogen atom or a $C_{1-6}$ alkyl group.

Process 9

Compound (IJ) can also be prepared by reacting Compound (1) with Compound (6) in an inert solvent and then reacting with a reductant in the presence or absence of acetic acid. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the reductant, sodium borohydride, sodium cyanoborohydride, sodium triacetoxyborohydride, 2-picoline borane or the like can be illustrated. The reaction temperature is usually at 0° C. to reflux temperature. The reaction time is usually from 10 minutes to 7 days, varying based on a used starting material, solvent and reaction temperature or the like.

A compound represented by the formula (IK) can be prepared, for example, by a method described in Process 10 of Scheme 10.

Scheme 10

[Chem. 18]

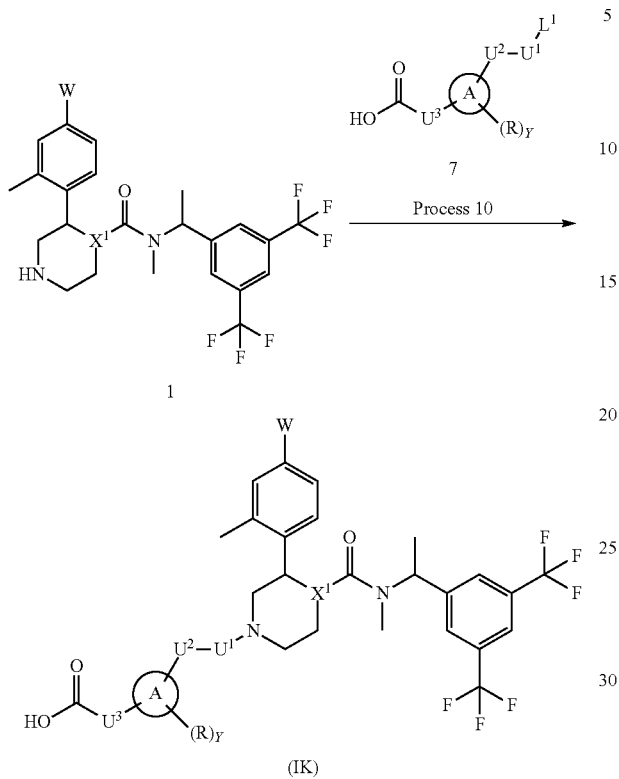

(IK)

In the formula, W, R, Y, $X^1$ and $U^3$ have the same meanings as defined above. Ring A is a group selected from the group consisting of above (a), (b), (c) and (d). $U^1$ is a methylene which may have any substituent selected from substituent group α and $U^2$ is a methylene which may have any substituent selected from substituent group α. $L^1$ represents a leaving group such as a chlorine atom, a bromine atom, an iodine atom and the like.

Process 10

Compound (IK) can also be prepared by reacting Compound (1) with Compound (7) in an inert solvent in the presence or absence of a base. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. The reaction temperature is usually at 0° C. to reflux temperature. The reaction time is usually from 30 minutes to 7 days, varying based on a used starting material, solvent and reaction temperature or the like.

In the compound (1), compound (1-1) wherein $X^1$ is a carbon atom can be prepared, for example, by a method described in Process 11 to 17 of Scheme 11.

Scheme 11

[Chem. 19]

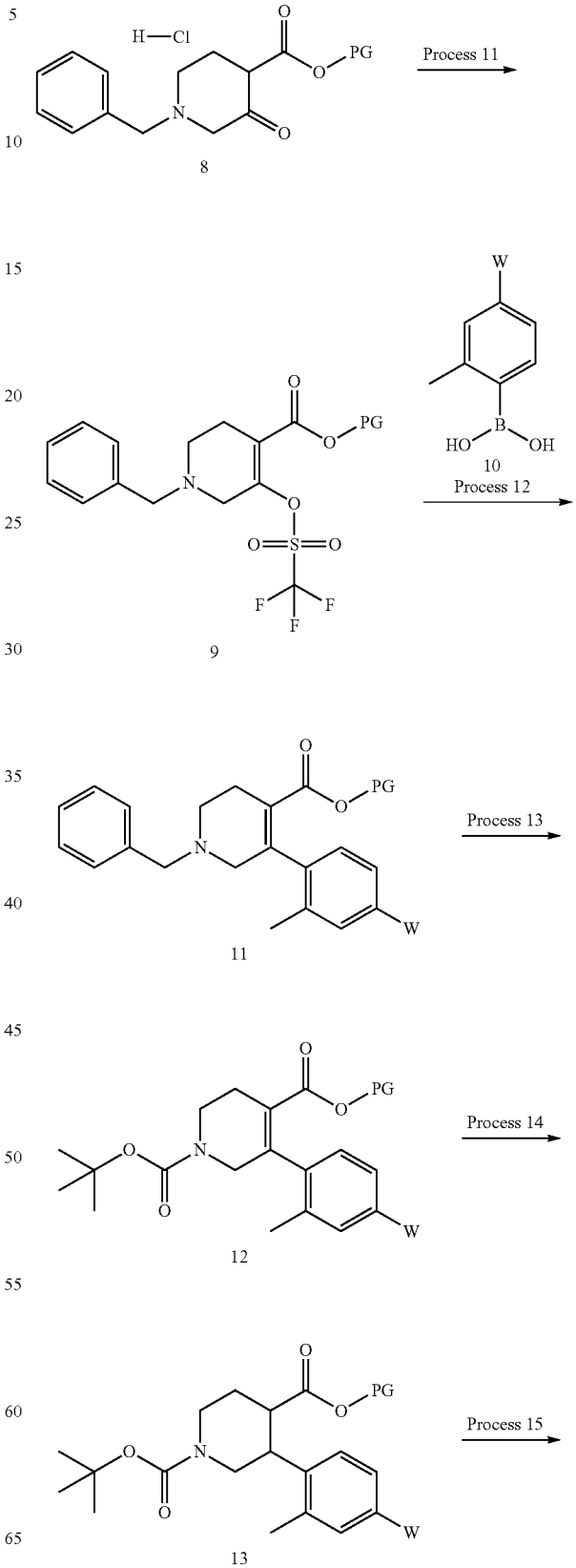

-continued

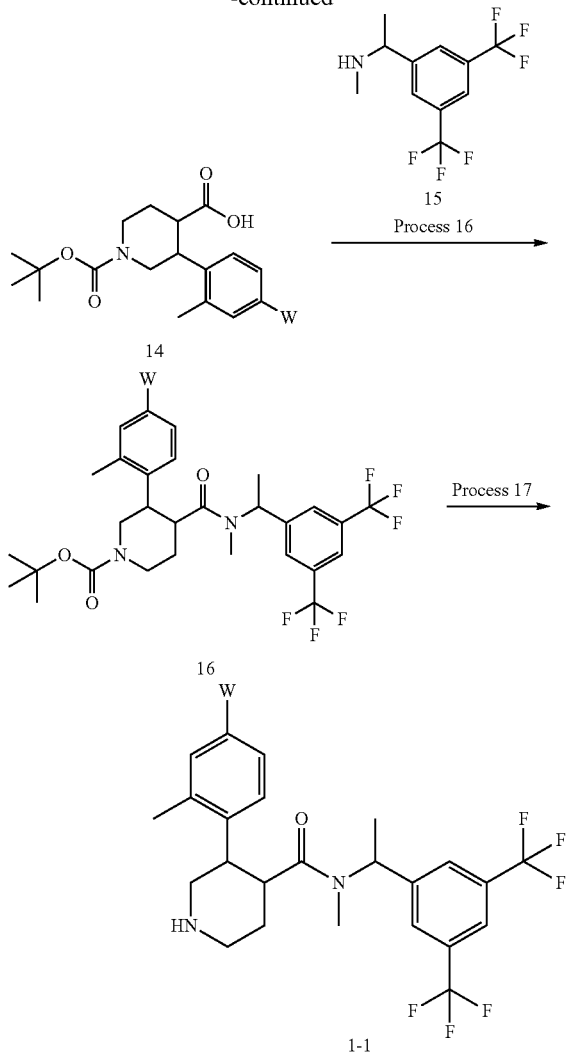

In the formula, W has the same meanings as defined above. PG represents a protective group.

Process 11

Compound (9) can also be prepared by reacting Compound (8) with a base in an inert solvent and then reacting with a trifluoromethanesulfonyl reagent. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, triethylamine, pyridine, N,N-diisopropylethylamine, 2,6-lutidine, 2,6-di-tert-butylpyridine, sodium hydroxide, lithium diisopropylamide, sodium bis(trimethylsilyl)amide, lithium bis(trimethylsilyl)amide, potassium bis(trimethylsilyl)amide, and the like can be illustrated. As the trifluoromethanesulfonyl reagent, trifluoromethanesulfonic anhydride, N-phenyl-bis(trifluoromethanesulfonimide), N-(5-Chloro-2-pyridyl)triflimide and the like can be illustrated. The reaction temperature is usually at −78° C. to reflux temperature. The reaction time is usually from 10 minutes to 7 days, varying based on a used starting material, solvent and reaction temperature or the like.

Process 12

Compound (11) can also be prepared by conducting coupling reaction of Compound (9) with Compound (10) in an inert solvent in the presence of a base and a palladium catalyst. As the inert solvent, for example, N,N-dimethylformamide, N-methylpyrrolidone, dimethyl sulfoxide, diethyl ether, tetrahydrofuran, 1,4-dioxane, 1,2-dimethoxyethane, benzene, toluene, xylene, ethanol, water and a mixed solvent thereof can be illustrated. As the base, for example, potassium carbonate, sodium carbonate, cesium carbonate, sodium hydroxide, potassium hydroxide, lithium hydroxide, potassium fluoride, cesium fluoride, triethylamine, pyridine, N,N-diisopropylethylamine, 2,6-lutidine, and 1,8-diazabicyclo[5.4.0]-7-undecene and the like can be illustrated. As the palladium catalyst, 1,1'-bis (diphenylphosphino) ferrocene-palladium (II) dichloride-dichloromethane complex (1:1), tetrakis(triphenylphosphine)palladium (0) and the like can be illustrated. The reaction temperature is usually at 0° C. to reflux temperature. The reaction time is usually from 30 minutes to 7 days, varying based on a used starting material, solvent and reaction temperature or the like. The above coupling reaction can also be conducted by using a microwave reactor (Biotage). When a microwave reactor is used, the reaction is conducted at pressure range: 1 to 30 bar, power range: 1 to 400 W, reaction temperature: room temperature to 300° C., and reaction time: a minute to 1 day, varying based on a used starting material, solvent and model or the like.

Process 13

Compound (12) can also be prepared by deprotecting a benzyl group of Compound (11) and then protecting it with a tert-butoxycarbonyl group.

Process 14

Compound (13) can also be prepared by reducing olefins of Compound (12) by a catalytic reduction method or the like. The catalytic reduction method can be conducted, for example, by allowing Compound (12) to react by using a catalyst under a hydrogen gas atmosphere in an inert solvent. As the inert solvent, for example, methanol, ethanol, ethyl acetate, tetrahydrofuran, acetic acid can be illustrated. As the catalyst, for example, palladium-carbon powder, rhodium-carbon powder, platinum-carbon powder, platinum oxide (IV), platinum-carbon powder doped with vanadium can be illustrated. The reaction temperature is usually at room temperature to reflux temperature. The reaction time is usually from 30 minutes to 7 days, varying based on a used starting material, solvent and reaction temperature or the like.

Process 15

Compound (14) can also be prepared by conducting alkaline hydrolysis of Compound (13) in an inert solvent. As the inert solvent, methanol, ethanol, tetrahydrofuran, 1,4-dioxane, water, a mixed solvent thereof and the like can be illustrated. As the base, sodium hydroxide, potassium hydroxide, lithium hydroxide, sodium methoxide, sodium ethoxide and the like can be used. The reaction temperature is, usually at 0° C. to reflux temperature. The reaction time is usually from 30 minutes to 7 days, varying based on a used starting material, solvent and reaction temperature or the like. Alternative to the alkaline hydrolysis, Compound (14) can also be prepared by conducting acid hydrolysis or hydrogenolysis.

Process 16

Compound (16) can also be prepared by reacting Compound (14) with Compound (15) by using a condensation reagent in an inert solvent. As the inert solvent, N,N-dimethylformamide, N-methylpyrrolidone, dimethyl sulfoxide, tetrahydrofuran, 1,4-dioxane, 1,2-dimethoxyethane, benzene, toluene, xylene, a mixed solvent thereof and the like can be illustrated. As the base, potassium carbonate, sodium carbonate, cesium carbonate, sodium hydroxide, potassium hydroxide, lithium hydroxide, triethylamine, pyridine, N,N-diisopropylethylamine, 2,6-lutidine, and 1,8-diazabicyclo[5.4.0]-7-undecene and the like can be illustrated. As the condensation reagent, CDI, HOBt, DCC, WSCD.HCl, PyBOP®, PyBroP®, HATU, HBTU and the like can be illustrated. The reaction temperature is usually at 0° C. to reflux temperature. The reaction time is usually from 30 minutes to 7 days, varying based on a used starting material, solvent and reaction temperature or the like.

Process 17

Compound (1-1) can also be prepared by deprotecting a tert-butoxy carbonyl group of Compound (16).

The above-mentioned schemes are exemplary for preparing compounds represented by the formula (I) of the present invention and synthetic intermediates thereof. The above schemes can be changed or modified into schemes which a person ordinarily skilled in the art can easily understand.

In the above schemes, a salt of Compound (1) can also be used as a starting material instead of Compound (1). When the salt of Compound (1) is used, reaction can also be conducted by adding a base and the like for use as a free form.

In the above schemes, when a protective group is necessary based on variation of functional group, the operations of introduction and remove can also be conducted optionally in combination according to a general method.

Compounds represented by the formula (I) of the present invention and intermediates thereof can also be isolated and purified, if required, according to conventional isolation and purification techniques well known to a person ordinarily skilled in the art in the relevant field, such as solvent extraction, crystallization, recrystallization, chromatography, preparative high performance liquid chromatography or the like.

The compounds of the present invention have an excellent $NK_1$ receptor antagonist activity, and thus can also be used as an agent for the prevention or treatment of various diseases mediated by $NK_1$ receptor. For example, the compounds of the present invention are useful as antiemetic agent, especially useful as preventive agent of cancer-chemotherapy (for example, cisplatin)-induced gastrointestinal symptom (for example, nausea and vomiting). Preferable compounds of the present invention are not only useful for acute cancer-chemotherapy-induced nausea and vomiting but also delayed cancer-chemotherapy-induced nausea and vomiting.

In an embodiment, the compounds of the present invention have an excellent $NK_1$ receptor antagonist activity, and thus can also be used as an agent for the prevention of postoperative nausea and vomiting (PONV), nausea and vomiting associated with radiotherapy, morphine-induced vomiting or motion sickness, and the treatment of schizophrenia, social phobia, anxiety and depression, alcoholism, irritable bowel syndrome, ulcerative colitis, coughing, asthma, atopic dermatitis, psoriasis, pruritus, pain, migraine, tinnitus, benign prostatic hyperplasia, overactive bladder or urinary incontinence.

Pharmaceutical compositions of the present invention can be administered in various dosage forms depending on their usages. As such dosage forms, for example, powders, granules, fine granules, dry syrups, tablets, capsules, injections, liquids, ointments, suppositories and poultices can be illustrated, which can be administered orally or parenterally.

Pharmaceutical compositions of the present invention can be prepared by using a compound represented by the formula (I) or a pharmaceutically acceptable salt thereof and at least one of a pharmaceutical additive. These pharmaceutical compositions can be formulated by admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents, solubilizing agents and the like, according to a conventional formulation procedure depending upon their dosage forms.

When a pharmaceutical composition of the present invention is used in the prevention or treatment, the dosage of a compound represented by the formula (I) or a pharmaceutically acceptable salt thereof as the active ingredient is appropriately decided to depend on the age, sex, body weight, degree of disorders and treatment of each patient and the like. The dosage for an adult can be decided within the range of, for example, 0.1 to 1000 mg per day, 0.1 to 500 mg per day, 0.1 to 100 mg per day, or 0.1 to 50 mg per day in the case of oral administration, and the daily dose can be divided into one, two, three or four times per day and administered. And, the dosage for an adult can be decided within the range of, for example, 0.1 to 1000 mg per day, 0.1 to 500 mg per day, 0.1 to 100 mg per day, or 0.1 to 50 mg per day in the case of parenteral administration, and the daily dose can be divided into one, two, three or four times per day and administered.

When a pharmaceutical composition of the present invention is used in the prevention of cancer-chemotherapy-induced nausea and vomiting, this pharmaceutical can also be administered before administration of antineoplastic agents. For example, the pharmaceutical can be administered immediately before administration to before an hour and a half of the administration in chemotherapy, and after the second day, the pharmaceutical can also be administered in the morning.

In an embodiment, a compound represented by the formula (I) of the present invention or a pharmaceutically acceptable salt thereof can also be used in combination with any other medicament other than $NK_1$ receptor antagonists. As such other medicaments used in combination, for example, corticosteroid and $5-HT_3$ receptor antagonist antiemetic agent can be illustrated.

When a compound represented by the formula (I) of the present invention or a pharmaceutically acceptable salt thereof are used in combination with the other medicament, it can be administered as a formulation comprising together with these active ingredients or as formulations each of which is separately formulated from each active ingredient. When separately formulated, these formulations can be administered separately or concurrently.

Furthermore, the dosage of the compound represented by the formula (I) of the present invention or a pharmaceutically acceptable salt thereof can be reduced depending on the dosage of the other medicaments used in combination.

EXAMPLES

The present invention is further illustrated in more detail by way of the following Reference Examples, Examples and Test Examples. However, the present invention is not limited thereto.

Reference Example 1

{4-[(S)-4-{[(R)-1-(3,5-Bistrifluoromethylphenyl)ethyl]methylcarbamoyl}-3-(4-fluoro-2-methylphenyl)piperazin-1-yl]cyclohexyl}acetic acid methyl ester A solution of (S)-2-(4-fluoro-2-methylphenyl)piperazine-1-carboxylic acid [(R)-1-(3,5-bistrifluoromethylphenyl)

ethyl]methylamide methanesulfonate (1:1) (0.059 g), 4-oxo-cyclohexyl)acetic acid methyl ester (0.026 g) and triethylamine (0.020 g) in tetrahydrofuran (3 mL) was stirred at room temperature for 10 minutes. To the reaction mixture were added sodium triacetoxyborohydride (0.042 g) and acetic acid (0.012 g) at room temperature, and the mixture was stirred at the same temperature overnight. To the reaction mixture was added a saturated aqueous solution of sodium bicarbonate, and the resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate/methanol) to give the title compound (0.050 g).

Reference Examples 2 and 3 cis-4-Ethoxycarbonylmethylcyclohexanecarboxylic acid benzyl ester (Reference Example 2) and trans-4-ethoxycarbonylmethylcyclohexanecarboxylic acid benzyl ester (Reference Example 3)

To a solution of 4-ethoxycarbonylmethylcyclohexanecarboxylic acid (8.96 g) in dichloromethane (50 mL) was added N,N-dimethylformamide (0.010 mL), and oxalyl chloride (10.62 g) was added dropwise to the resulting mixture at room temperature, and the mixture was stirred at the same temperature for 2 hours. The reaction mixture was concentrated under reduced pressure, and to the residue was added dichloromethane and then concentrated again. This step was repeated 3 times. To the obtained residue was added dichloromethane (50 mL) and triethylamine (6.35 g), and to the resulting mixture was added dropwise benzyl alcohol (5.43 g) under ice-cooling, and the mixture was stirred at room temperature overnight. To the reaction mixture was added a saturated aqueous solution of sodium bicarbonate, and the resulting mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate) to give both Reference Example 2 (2.51 g) and Reference Example 3 (3.43 g). In the above chromatography, the compound of Reference Example 2 was in the low polarity side, and the compound of Reference Example 3 was in the high polarity side.

Reference Example 4 cis-4-Ethoxycarbonylmethylcyclohexanecarboxylic acid

Under a hydrogen gas atmosphere, a suspension of cis-4-ethoxycarbonylmethylcyclohexanecarboxylic acid benzyl ester (2.51 g) and 10% palladium on carbon (0.30 g, wet) in ethanol (20 mL) was stirred at room temperature overnight. The reaction mixture was filtered through a Celite® pad, and the filtrate was concentrated under reduced pressure to give the title compound (1.81 g).

Reference Example 5

The compound of Reference Example 5 was prepared in a similar manner to that described in Reference Example 4 using the corresponding starting material.

Reference Example 6 cis-{4-[(S)-4-{[(R)-1-(3,5-Bistrifluoromethylphenyl)ethyl]methylcarbamoyl}-3-(4-fluoro-2-methylphenyl)piperazine-1-carbonyl]cyclohexyl}acetic acid ethyl ester To a solution of (S)-2-(4-fluoro-2-methylphenyl)piperazine-1-carboxylic acid [(R)-1-(3,5-bistrifluoromethylphenyl)ethyl]methylamide methanesulfonate (0.059 g), cis-4-ethoxycarbonylmethylcyclohexanecarboxylic acid (0.032 g) and N,N-diisopropylethylamine (0.039 g) in N,N-dimethylformamide was added O-(7-aza-benzotriazol-1-yl)-N,N,N',N'-tetramethyluronium hexafluorophosphate (0.076 g) at room temperature, and the mixture was stirred at the same temperature overnight. Water was added to the reaction mixture, and extracted twice with ethyl acetate. The combined organic layer was washed twice with brine, and dried over anhydrous magnesium sulfate, and the solvent was removed under reduced pressure. The obtained crude product was purified by column chromatography on silica gel (eluent: n-hexane/ethyl acetate=80/20-0/100) to give the title compound (0.070 g).

Reference Example 7

The compound of Reference Example 7 was prepared in a similar manner to that described in Reference Example 6 using the corresponding starting material.

Reference Example 8 cis-(4-Hydroxymethylcyclohexyl)acetic acid ethyl ester

Under an argon gas atmosphere, to a solution of cis-4-ethoxycarbonylmethylcyclohexanecarboxylic acid (0.43 g) in tetrahydrofuran (10 mL) was added dropwise borane-tetrahydrofuran complex (1.0 mol/L in tetrahydrofuran solution, 3.0 mL). After the mixture was stirred at room temperature overnight, water was added to the mixture at the same temperature. To the mixture was added brine, and extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=60/40-0/100) to give the title compound (0.33 g).

Reference Example 9

The compound of Reference Example 9 was prepared in a similar manner to that described in Reference Example 8 using the corresponding starting material.

Reference Example 10 cis-(4-Formylcyclohexyl)acetic acid ethyl ester

To a solution of cis-(4-hydroxymethylcyclohexyl)acetic acid ethyl ester (0.33 g) in dichloromethane (10 mL) was added Dess-Martin periodinane (0.85 g) under ice-cooling, and the mixture was stirred at room temperature for 4 hours. The reaction mixture was diluted with ethyl acetate, and the resulting mixture was washed with 1.0 mol/L aqueous sodium hydroxide solution and brine. The organic layer was dried over anhydrous magnesium sulfate, and the solvent was removed under reduced pressure. The obtained crude product was purified by column chromatography on silica gel (eluent: n-hexane/ethyl acetate=85/15-0/100) to give the title compound (0.20 g).

Reference Example 11

The compound of Reference Example 11 was prepared in a similar manner to that described in Reference Example 10 using the corresponding starting material.

Reference Examples 12 to 14

The compounds of Reference Examples 12 to 14 were prepared in a similar manner to that described in Reference Example 1 using the corresponding starting materials.

Reference Example 15 cis-4-Hydroxymethylcyclohexanecarboxylic acid methyl ester

To a solution of cis-cyclohexane-1,4-dicarboxylic acid monomethyl ester (1.0 g) in tetrahydrofuran (50 mL) was added borane-dimethyl sulfide complex (0.61 g) under ice-cooling, and the mixture was stirred at the same temperature for 15 minutes and at room temperature for 4 hours. To the reaction mixture was added methanol (0.17 g) at room temperature, and was stirred for 20 minutes, and the mixture was concentrated under reduced pressure. To the residue was added methyl tert-butyl ether (30 mL) at room temperature, and the mixture was stirred for a while, and the insoluble material was removed by filtration through a Celite® pad, and the filtrate was concentrated under reduced pressure. To the residue was added 1.0 mol/L aqueous sodium hydroxide solution, and the mixture was extracted with ethyl acetate. The organic layer was washed with water and brine. The organic layer was dried over anhydrous magnesium sulfate, and the solvent was removed under reduced pressure to give the title compound (0.87 g).

Reference Example 16

The compound of Reference Example 16 was prepared in a similar manner to that described in Reference Example 15 using the corresponding starting material.

Reference Example 17 cis-4-Formylcyclohexanecarboxylic acid methyl ester

Under an argon gas atmosphere, to a solution of dimethyl sulfoxide (0.90 g) in dichloromethane (40 mL) was added oxalyl chloride (0.73 g) at −78° C., and the mixture was stirred at the same temperature for 5 minutes. To the reaction mixture was added dropwise a solution of cis-4-hydroxymethylcyclohexanecarboxylic acid methyl ester (0.83 g) in dichloromethane (10 mL) at −78° C., and the mixture was stirred at the same temperature for 30 minutes. To the reaction mixture was added triethylamine (2.43 g) at −78° C., and stirred at the same temperature for 15 minutes. To the reaction mixture was added 1.0 mol/L hydrochloric acid (15 mL) under ice-cooling, and the organic layer was separated. The organic layer was washed with water and brine, and dried over anhydrous magnesium sulfate, and the solvent was removed under reduced pressure to give the title compound (0.78 g).

Reference Example 18

The compound of Reference Example 18 was prepared in a similar manner to that described in Reference Example 17 using the corresponding starting material.

Reference Examples 19 and 20

The compounds of Reference Examples 19 and 20 were prepared in a similar manner to that described in Reference Example 1 using the corresponding starting materials.

Reference Example 21

{4-[(S)-4-{[(R)-1-(3,5-Bistrifluoromethylphenyl) ethyl]methylcarbamoyl}-3-(4-fluoro-2-methylphenyl)piperazin-1-ylmethyl]phenyl}acetic acid methyl ester To a solution of (S)-2-(4-fluoro-2-methylphenyl)piperazine-1-carboxylic acid [(R)-1-(3,5-bistrifluoromethylphenyl)ethyl]methylamide methanesulfonate (0.080 g) in N,N-dimethylformamide (0.32 mL) was added N,N-diisopropylethylamine (0.039 g) at room temperature, and the mixture was stirred at the same temperature for 30 minutes. To the reaction mixture was added a solution of (4-bromomethylphenyl)acetic acid methyl ester (0.036 g) in N,N-dimethylformamide (0.15 mL) under ice-cooling, and the mixture was stirred at room temperature for 30 minutes. To the reaction mixture was added water, and the resulting mixture was extracted with ethyl acetate. The organic layer was dried over anhydrous magnesium sulfate, and the solvent was removed under reduced pressure. The residue was purified by column chromatography on aminopropylated silica gel (eluent: n-hexane/ethyl acetate) to give the title compound (0.086 g).

Reference Example 22

4-Ethoxycarbonylmethylpiperidine-1-carboxylic acid 4-nitrophenyl ester

To a solution of piperidin-4-ylacetic acid ethyl ester (0.20 g) in tetrahydrofuran (18 mL) was added 4-nitrophenyl chloroformate (0.26 g) and triethylamine (0.36 g) at room temperature, and the mixture was stirred at the same temperature for 12 hours. The reaction mixture was filtered, and the filtrate was concentrated under reduced pressure. The residue was purified by column chromatography on silica gel (eluent: n-hexane/ethyl acetate) to give the title compound (0.33 g).

Reference Example 23

{1-[(S)-4-{[(R)-1-(3,5-Bistrifluoromethylphenyl) ethyl]methylcarbamoyl}-3-(4-fluoro-2-methylphenyl)piperazine-1-carbonyl]piperidin-4-yl}acetic acid ethyl ester To a solution of (S)-2-(4-fluoro-2-methylphenyl)piperazine-1-carboxylic acid [(R)-1-(3,5-bistrifluoromethylphenyl)ethyl]methylamide methanesulfonate (0.051 g) in N,N-dimethylformamide (0.50 mL) was added triethylamine (0.017 g) at room temperature, and the mixture was stirred at the same temperature for 30 minutes. To the reaction mixture was added 4-ethoxycarbonylmethylpiperizine-1-caroxylic acid 4-nitrophenyl ester (0.043 g) at room temperature, and the mixture was stirred at 120° C. for 15 hours. The reaction mixture was cooled to room temperature and water was added. The resulting mixture was extracted with ethyl acetate. The aqueous layer was re-extracted with ethyl acetate. The combined organic layer was dried over anhydrous magnesium sulfate, and the solvent was removed under reduced pressure. The residue was purified by column chromatography on aminopropylated silica gel (eluent: n-hexane/ethyl acetate) to give the title compound.

Reference Example 24

3-[(S)-4-{[(R)-1-(3,5-Bistrifluoromethylphenyl)ethyl]methylcarbamoyl}-3-(4-fluoro-2-methylphenyl)piperazin-1-yl methyl]bicyclo[1.1.1]pentane-1-carboxylic acid methyl ester To a solution of (S)-2-(4-fluoro-2-methylphenyl)piperazine-1-carboxylic acid [(R)-1-(3,5-bistrifluoromethylphenyl)ethyl]methylamide methanesulfonate (0.12 g) and 3-formylbicyclo[1.1.1]pentane-1-carboxylic acid methyl ester (0.049 g) in tetrahydrofuran (5.3 mL) was added N,N-diisopropylethylamine (0.055 g) at room temperature, and the mixture was stirred at the same temperature for 30 minutes. To the reaction mixture was added sodium triacetoxyborohydride (0.090 g) and acetic acid (0.026 g) at room temperature, and the mixture was stirred at the same temperature for 12 hours. To the reaction mixture was added a saturated aqueous solution of sodium bicarbonate, and the resulting mixture was extracted with ethyl acetate. The extract was dried over anhydrous magnesium sulfate, and the solvent was removed under reduced pressure. The residue was purified by column chromatography on aminopropylated silica gel (eluent: n-hexane/ethyl acetate) to give the title compound (0.048 g).

Reference Example 25

1-Benzyl-5-(4-fluoro-2-methylphenyl)-1,2,3,6-tetrahydropyridine-4-carboxylic acid ethyl ester To a suspension of sodium hydride (60%, 0.67 g) in N,N-dimethylformamide (15 mL) was added 1-benzyl-3-oxopiperizine-4-carboxylic acid ethyl ester hydrochloride (2.0 g) under ice-cooling, and the mixture was stirred under ice-cooling for 5 minutes. To the reaction mixture was added N-phenylbis(trifluoromethanesulfonimide) (2.64 g) under ice-cooling, and the mixture was stirred at room temperature for 2 hours. To the reaction mixture was added water, and the resulting mixture was extracted with ethyl acetate. The organic layer was washed with a saturated aqueous ammonium chloride solution and brine, and dried over anhydrous magnesium sulfate, and the solvent was removed under reduced pressure. The obtained crude product was purified by column chromatography on silica gel (eluent: n-hexane/ethyl acetate=91/9-50/50) to give 1-benzyl-5-trifluoromethanesulfonyloxy-1,2,3,6-tetrahydropyridine-4-caroboxylic acid ethyl ester (2.82 g). Under an argon gas atmosphere, to a mixture of 1-benzyl-5-trifluoromethanesulfonyloxy-1,2,3,6-tetrahydropyridine-4-caroboxylic acid ethyl ester (2.82 g), 4-fluoro-2-methylphenyl boronic acid (1.55 g), toluene (20 mL) and water (2 mL) were added tetrakis(triphenylphosphine)palladium(0) (0.39 g) and potassium carbonate (0.93 g) at room temperature, and the mixture was stirred at 100° C. overnight. The reaction mixture was cooled to room temperature and water was added. The resulting mixture was extracted with ethyl acetate. The organic layer was washed with a saturated aqueous ammonium chloride solution and brine, and dried over anhydrous magnesium sulfate, and the solvent was removed under reduced pressure. The obtained crude product was purified by column chromatography on silica gel (eluent: n-hexane/ethyl acetate=91/9-50/50) to give the title compound (2.29 g).

Reference Example 26

5-(4-Fluoro-2-methylphenyl)-1,2,3,6-tetrahydropyridine-4-carboxylic acid ethyl ester hydrochloride To a solution of 1-benzyl-5-(4-fluoro-2-methylphenyl)-1,2,3,6-tetrahydropyridine-4-caroboxylic acid ethyl ester (2.29 g) in ethyl acetate (20 mL) was added a hydrogen chloride solution (4.0 mol/L ethyl acetate solution, 1.78 mL) at toom temperature. To the reaction mixture was added n-hexane (20 mL), and the mixture was stirred at the same temperature for 1 hour. The precipitated crystals were collected by filtration, and dried under reduced pressure to give the crude product. To the mixture of the crude product, ethanol (75 mL) and methanol (15 mL) was added 10% palladium on carbon (0.8 g, wet) at room temperature, and the resulting mixture was stirred under a hydrogen gas atmosphere at room temperature overnight. The reaction mixture was filtered through a Celite® pad, and the filtrate was concentrated under reduced pressure to give the title compound (1.98 g).

Reference Example 27

5-(4-Fluoro-2-methylphenyl)-3,6-dihydro-2H-pyridine-1,4-dicarboxylic acid 1-tert-butyl 4-ethyl ester To a solution of 5-(4-fluoro-2-methylphenyl)-1,2,3,6-tetrahydropyridine-4-caroboxylic acid ethyl ester hydrochloride (1.94 g) and triethylamine (1.44 g) in acetonitrile (50 mL) was added di-tert-butyl dicarbonate (2.12 g) at room temperature, and the mixture was stirred at the same temperature for 2 days. The reaction mixture was concentrated under reduced pressure. To the residue was added water, and extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=95/5-50/50) to give the title compound (1.70 g).

Reference Example 28

3-(4-Fluoro-2-methylphenyl)piperidine-1,4-dicarboxylic acid 1-tert-butyl 4-ethyl ester Under a hydrogen gas atmosphere, a suspension of 5-(4-fluoro-2-methylphenyl)-3,6-dihydro-2H-pyridine-1,4-dicaroboxylic acid 1-tert-butyl 4-ethyl ester (1.69 g) and platinum oxide (IV) (0.21 g) in acetic acid (8 mL) was stirred at room temperature for 24 hours. The reaction mixture was filtered through a Celite® pad, and the filtrate was concentrated under reduced pressure. To the residue was added toluene, and then the solvent was removed azeotropically twice. To the residue was added a saturated aqueous solution of sodium bicarbonate, and the mixture was extracted with ethyl acetate. The organic layer was washed with brine, and dried over anhydrous magnesium sulfate, and the solvent was removed under reduced pressure. The obtained crude product was purified by column chromatography on silica gel (eluent: n-hexane/ethyl acetate=95/5-50/50) to give the title compound (0.62 g).

Reference Example 29

3-(4-Fluoro-2-methylphenyl)piperidine-1,4-dicarboxylic acid 1-tert-butyl ester

To a solution of 3-(4-fluoro-2-methylphenyl)piperizine-1,4-dicaroboxylic acid 1-tert-butyl 4-ethyl ester (0.62 g) in methanol (8 mL) was added sodium methoxide (28% methanol solution, 0.66 mL) at room temperature, and the mixture was heated under reflux for 5 hours. To the reaction mixture were added 1.0 mol/L aqueous sodium hydroxide solution (5.1 mL) and tetrahydrofuran (20 mL), and the mixture was stirred at 60° C. overnight. To the reaction mixture were added 1.0 mol/L hydrochloric acid (10 mL) and brine, and the resulting mixture was extracted with ethyl acetate. The aqueous layer was re-extracted with ethyl acetate. The combined organic layer was washed twice with water and brine twice, and dried over anhydrous magnesium sulfate, and the solvent was removed under reduced pressure to give the title compound (0.59 g).

Reference Example 30

[(S)-1-(3,5-Bistrifluoromethylphenyl)ethyl]methylamine D-(+)-malate

Under an argon gas atmosphere, to a solution of 1-(3,5-bistrifluoromethylphenyl)ethanone (10.25 g) in methanol (15 mL) was added methylamine (9.8 mol/L methanol solution, 10.2 mL) at room temperature, and the mixture was stirred at room temperature for 24 hours. To the reaction mixture was added sodium borohydride (0.95 g) under ice-cooling, and the mixture was stirred at the same temperature for 30 minutes. To the reaction mixture was added sodium borohydride (0.58 g) under ice-cooling, and the mixture was stirred at the same temperature for 4 hours. The reaction mixture was concentrated under reduced pressure, and to the residue was added a saturated aqueous ammonium chloride solution, and the mixture was extracted with ethyl acetate. The aqueous layer was re-extracted with ethyl acetate. The combined organic layer was washed with brine, and dried over anhydrous magnesium sulfate, and the solvent was removed under reduced pressure to give the residue. To the obtained residue was added ethyl acetate (90 mL) to dissolve, and to the mixture was added L-(−)-malic acid (4.83 g) at room temperature, and the mixture was stirred at the same temperature overnight. The obtained suspension was stirred under ice-cooling for 3 hours. After the crystals were collected by filtration, a saturated aqueous solution of sodium carbonate was added to the filtrate, and the mixture was extracted with ethyl acetate. The organic layer was washed with brine, and dried over anhydrous magnesium sulfate, and the solvent was removed under reduced pressure to give the residue. To a solution of the residue in ethyl acetate (55 mL) was added D-(+)-malic acid (3.21 g) at room temperature, and the mixture was stirred at the same temperature for 3 hours. The precipitated crystals were collected by filtration, and dried under reduced pressure. The obtained crude crystals were dissolved by heating in ethyl acetate (65 mL), and the solution was stirred at room temperature for 1 hour and under ice-cooling for 1.5 hours. The precipitated crystals were collected by filtration, and dried under reduced pressure to give the title compound (4.76 g).

Reference Example 31

(3 S,4S)-4-{[(S)-1-(3,5-Bistrifluoromethylphenyl)ethyl]methylcarbamoyl}-3-(4-fluoro-2-methylphenyl)piperidine-1-carboxylic acid tert-butyl ester To [(S)-1-(3,5-bistrifluoromethylphenyl)ethyl]methylamine D-(+)-malate (1.03 g) was added a saturated aqueous sodium carbonate solution, and the mixture was extracted with ethyl acetate. The aqueous layer was re-extracted with ethyl acetate. The combined organic layer was washed with brine, and dried over anhydrous sodium sulfate, and the solvent was removed under reduced pressure. After the residue was dissolved in N,N-dimethylformamide, 3-(4-fluoro-2-methylphenyl)piperizine-1,4-dicaroboxylic acid 1-tert-butyl ester (0.57 g), N,N-diisopropylethylamine (0.66 g) and O-(7-azabenzotriazol-1-yl)-N,N,N',N'-tetramethyluronium hexafluorophosphate (1.29 g) were added to the mixture at room temperature, and the mixture was stirred at the same temperature overnight. To the reaction mixture was added water, and the resulting mixture was extracted with ethyl acetate. The aqueous layer was re-extracted with ethyl acetate. The combined organic layer was washed with brine, and dried over anhydrous magnesium sulfate, and the solvent was removed under reduced pressure. The obtained crude product was purified by column chromatography on silica gel (eluent: n-hexane/ethyl acetate=95/5-50/50) to give the title compound (0.39 g).

Reference Example 32

(3S,4S)-3-(4-Fluoro-2-methylphenyl)piperidine-4-carboxylic acid [(S)-1-(3,5-bistrifluoromethylphenyl)ethyl]methylamide hydrochloride To a solution of (3S,4S)-4-{[(S)-1-(3,5-bistrifluoromethylphenyl)ethyl]methyl carbamoyl}-3-(4-fluoro-2-methylphenyl)piperizine-1-caroboxylic acid tert-butyl ester (0.39 g) in ethanol (5 mL) was added a solution of 4 mol/L hydrogen chloride in ethyl acetate (0.66 mL) at room temperature, and the mixture was stirred at 50° C. for 5 hours. After the reaction mixture was cooled to room temperature, the solvent was concentrated under reduced pressure. To the residue were added ethyl acetate and diethyl ether, and then the precipitated crystals were collected by filtration, and dried under reduced pressure to give the title compound (0.23 g).

Reference Examples 33 to 35

The compounds of Reference Examples 33 to 35 were prepared in a similar manner to that described in Reference Example 1 using the corresponding starting materials.

Example 1

{4-[(S)-4-{[(R)-1-(3,5-Bistrifluoromethylphenyl)ethyl]methylcarbamoyl}-3-(4-fluoro-2-methylphenyl)piperazin-1-yl]cyclohexyl}acetic acid To a mixture of {4-[(S)-4-{[(R)-1-(3,5-bistrifluoromethylphenyl)ethyl]methyl-carbamoyl}-3-(4-fluoro-2-methylphenyl)piperazin-1-yl]cyclohexyl}acetic acid methyl ester (0.043 g), tetrahydrofuran (1 mL), methanol (1 mL) and water (0.3 mL) was added lithium hydroxide monohydrate (0.014 g) at room temperature, and the mixture was stirred at the same temperature overnight. To the reaction mixture were added 1.0 mol/L hydrochloric acid (0.33 mL) and water, and the resulting mixture was extracted with ethyl acetate. The organic layer was dried over anhydrous magnesium sulfate. The solvent was concentrated under reduced pressure to give the title compound (0.03 g).

Example 2 cis-{4-[(S)-4-{[(R)-1-(3,5-Bistrifluoromethylphenyl) ethyl]methylcarbamoyl}-3-(4-fluoro-2-methylphenyl)piperazine-1-carbonyl]cyclohexyl}acetic acid To a mixture of cis-{4-[(S)-4-{[(R)-1-(3,5-bistrifluoromethylphenyl)ethyl]methylcarbamoyl}-3-(4-fluoro-2-methylphenyl)piperazine-1-carbonyl]cyclohexyl]acetic acid ethyl ester (0.066 g), tetrahydrofuran (1 mL), methanol (1 mL) and water (0.3 mL) was added lithium hydroxide monohydrate (0.048 g) at room temperature, and the mixture was stirred at the same temperature overnight. To the reaction mixture were added 1.0 mol/L hydrochloric acid (1.15 mL) and water, and the resulting mixture was extracted with ethyl acetate. The organic layer was dried over anhydrous magnesium sulfate. The solvent was concentrated under reduced pressure to give the title compound (0.06 g).

Example 3 trans-{4-[(S)-4-{[(R)-1-(3,5-Bistrifluoromethylphenyl)ethyl]methylcarbamoyl}-3-(4-fluoro-2-methylphenyl)piperazine-1-carbonyl]cyclohexyl}acetic acid To a mixture of trans-{4-[(S)-4-{[(R)-1-(3,5-bistrifluoromethylphenyl)ethyl]methylcarbamoyl}-3-(4-fluoro-2-methylphenyl)piperazine-1-carbonyl]cyclohexyl}acetic acid ethyl ester (0.062 g), tetrahydrofuran (1 mL), methanol (1 mL) and water (0.3 mL) was added lithium hydroxide monohydrate (0.019 g) at room temperature, and the mixture was stirred at the same temperature overnight. To the reaction mixture were added 1.0 mol/L hydrochloric acid (0.45 mL) and water, and the resulting mixture was extracted with ethyl acetate. The organic layer was dried over anhydrous magnesium sulfate. The solvent was concentrated under reduced pressure to give the title compound (0.04 g).

Example 4 cis-{4-[(S)-4-{[(R)-1-(3,5-Bistrifluoromethylphenyl) ethyl]methylcarbamoyl}-3-(4-fluoro-2-methyl phenyl)piperazin-1-ylmethyl]cyclohexyl}acetic acid To a mixture of cis-{4-[(S)-4-{[(R)-1-(3,5-bistrifluoromethylphenyl)ethyl]methylcarbamoyl}-3-(4-fluoro-2-methylphenyl)piperazin-1-ylmethyl]cyclohexyl}acetic acid ethyl ester (0.062 g), tetrahydrofuran (1 mL), methanol (1 mL) and water (0.3 mL) was added lithium hydroxide monohydrate (0.019 g) at room temperature, and the mixture was stirred at the same temperature overnight. To the reaction mixture were added 1.0 mol/L hydrochloric acid (0.46 mL) and water, and the resulting mixture was extracted with ethyl acetate. The organic layer was dried over anhydrous magnesium sulfate. The solvent was concentrated under reduced pressure to give the title compound (0.06 g).

Example 5 trans-{4-[(S)-4-{[(R)-1-(3,5-Bistrifluoromethylphenyl)ethyl]methylcarbamoyl}-3-(4-fluoro-2-methylphenyl)piperazin-1-ylmethyl]cyclohexyl}acetic acid To a mixture of trans-{4-[(S)-4-{[(R)-1-(3,5-bistrifluoromethylphenyl)ethyl]methylcarbamoyl}-3-(4-fluoro-2-methylphenyl)piperazin-1-ylmethyl]cyclohexyl}acetic acid ethyl ester (0.065 g), tetrahydrofuran (1 mL), methanol (1 mL) and water (0.3 mL) was added lithium hydroxide monohydrate (0.020 g) at room temperature, and the mixture was stirred at the same temperature overnight. To the reaction mixture were added 1.0 mol/L hydrochloric acid (0.45 mL) and water, and the resulting mixture was extracted with ethyl acetate. The organic layer was dried over anhydrous magnesium sulfate. The solvent was concentrated under reduced pressure to give the title compound (0.06 g).

Example 6

4-[(S)-4-{[(R)-1-(3,5-Bistrifluoromethylphenyl) ethyl]methylcarbamoyl}-3-(4-fluoro-2-methylphenyl)piperazin-1-yl]cyclohexanecarboxylic acid To a mixture of 4-[(S)-4-{[(R)-1-(3,5-bistrifluoromethylphenyl)ethyl]methyl carbamoyl}-3-(4-fluoro-2-methylphenyl)piperazin-1-yl]cyclohexanecarboxylic acid ethyl ester (0.040 g), tetrahydrofuran (1 mL), methanol (1 mL) and water (0.3 mL) was added lithium hydroxide monohydrate (0.026 g) at room temperature, and the mixture was stirred at the same temperature for 2 days. To the reaction mixture was added 2.0 mol/L hydrochloric acid (0.50 mL), and the mixture was extracted with ethyl acetate. The organic layer was washed with water and brine, and dried over anhydrous magnesium sulfate. The solvent was concentrated under reduced pressure to give the title compound (0.036 g).

Example 7 cis-4-[(S)-4-{[(R)-1-(3,5-Bistrifluoromethylphenyl) ethyl]methylcarbamoyl}-3-(4-fluoro-2-methylphenyl)piperazin-1-ylmethyl]cyclohexanecarboxylic acid To a mixture of cis-4-[(S)-4-{[(R)-1-(3,5-bistrifluoromethylphenyl)ethyl]methylcarbamoyl}-3-(4-fluoro-2-methylphenyl)piperazin-1-ylmethyl]cyclohexanecarboxylic acid methyl ester (0.053 g), tetrahydrofuran (1 mL), methanol (1 mL) and water (0.3 mL) was added lithium hydroxide monohydrate (0.035 g) at room temperature, and the mixture was stirred at the same temperature for 2 days. To the reaction mixture was added 2.0 mol/L hydrochloric acid (0.50 mL), and the mixture was extracted with ethyl acetate. The organic layer was washed with water and brine, and dried over anhydrous magnesium sulfate. The solvent was concentrated under reduced pressure to give the title compound (0.040 g).

Example 8 trans-4-[(S)-4-{[(R)-1-(3,5-Bistrifluoromethylphenyl)ethyl]methylcarbamoyl}-3-(4-fluoro-2-methylphenyl)piperazin-1-ylmethyl]cyclohexanecarboxylic acid To a mixture of trans-4-[(S)-4-{[(R)-1-(3,5-bistrifluoromethylphenyl)ethyl]methylcarbamoyl}-3-(4-fluoro-2-methylphenyl)piperazin-1-ylmethyl]cyclohexanecarboxylic acid methyl ester (0.058 g), tetrahydrofuran (1 mL), methanol (1 mL) and water (0.3 mL) was added lithium hydroxide monohydrate (0.038 g) at room temperature, and the mixture was stirred at the same temperature for 2 days. To the reaction mixture was added 2.0 mol/L hydrochloric acid (0.50 mL), and the mixture was extracted with ethyl acetate. The organic layer was washed with water and brine, and dried over anhydrous magnesium sulfate. The solvent was concentrated under reduced pressure to give the title compound (0.052 g).

Example 9

{4-[(S)-4-{[(R)-1-(3,5-Bistrifluoromethylphenyl)ethyl]methylcarbamoyl}-3-(4-fluoro-2-methylphenyl)piperazin-1-ylmethyl]phenyl}acetic acid To a mixture of {4-[(S)-4-{[(R)-1-(3,5-bistrifluoromethylphenyl)ethyl]methyl-carbamoyl}-3-(4-fluoro-2-methylphenyl)piperazin-1-ylmethyl]phenyl}acetic acid methyl ester (0.084 g), tetrahydrofuran (1 mL), methanol (0.5 mL) and water (0.5 mL) was added lithium hydroxide monohydrate (0.016 g) at room temperature, and the mixture was stirred at the same temperature for 11 hours. To the reaction mixture were added 2.0 mol/L hydrochloric acid (0.19 mL) and water, and the resulting mixture was extracted with ethyl acetate. The organic layer was dried over anhydrous magnesium sulfate. The solvent was concentrated under reduced pressure to give the title compound (0.081 g).

Example 10

{1-[(S)-4-{[(R)-1-(3,5-Bistrifluoromethylphenyl)ethyl]methylcarbamoyl}-3-(4-fluoro-2-methylphenyl)piperazine-1-carbonyl]piperidin-4-yl}acetic acid To a mixture of {1-[(S)-4-{[(R)-1-(3,5-bistrifluoromethylphenyl)ethyl]methyl-carbamoyl}-3-(4-fluoro-2-methylphenyl)piperazine-1-carbonyl]piperizin-4-yl}acetic acid ethyl ester (0.11 g), tetrahydrofuran (1.6 mL), methanol (0.8 mL) and water (0.8 mL) was added lithium hydroxide monohydrate (0.021 g) at room temperature, and the mixture was stirred at the same temperature for 4 hours. To the reaction mixture were added 2.0 mol/L hydrochloric acid (0.25 mL) and water, and the resulting mixture was extracted with ethyl acetate. The organic layer was dried over anhydrous magnesium sulfate. The solvent was concentrated under reduced pressure to give the title compound (0.10 g).

Example 11

3-[(S)-4-{[(R)-1-(3,5-Bistrifluoromethylphenyl)ethyl]methylcarbamoyl}-3-(4-fluoro-2-methylphenyl)piperazin-1-ylmethyl]bicyclo[1.1.1]pentane-1-carboxylic acid To a mixture of 3-[(S)-4-{[(R)-1-(3,5-bistrifluoromethylphenyl)ethyl]methyl-carbamoyl}-3-(4-fluoro-2-methylphenyl)piperazin-1-ylmethyl]bicyclo[1.1.1]pentane-1-carboxylic acid methyl ester (0.048 g), tetrahydrofuran (1 mL), methanol (0.5 mL) and water (0.5 mL) was added lithium hydroxide monohydrate (0.010 g) at room temperature, and the mixture was stirred at the same temperature for 4 hours. To the reaction mixture were added 2.0 mol/L hydrochloric acid (0.12 mL) and water, and the resulting mixture was extracted with ethyl acetate. The organic layer was dried over anhydrous magnesium sulfate. The solvent was concentrated under reduced pressure to give the title compound (0.050 g).

Example 12

{4-[(3 S,4S)-4-{[(S)-1-(3,5-Bistrifluoromethylphenyl)ethyl]methylcarbamoyl}-3-(4-fluoro-2-methylphenyl)piperidin-1-yl]cyclohexyl}lacetic acid To a mixture of {4-[(3S,4S)-4-{[(S)-1-(3,5-bistrifluoromethylphenyl)ethyl]-methylcarbamoyl}-3-(4-fluoro-2-methylphenyl)piperidin-1-yl]cyclohexyl}lacetic acid methyl ester (0.042 g), tetrahydrofuran (1 mL), methanol (1 mL) and water (0.3 mL) was added lithium hydroxide monohydrate (0.020 g) at room temperature, and the mixture was stirred at the same temperature overnight. To the reaction mixture were added 1.0 mol/L hydrochloric acid (0.47 mL) and water, and the resulting mixture was extracted with ethyl acetate. The organic layer was dried over anhydrous magnesium sulfate. The solvent was concentrated under reduced pressure to give the title compound (0.030 g).

Example 13 cis-{4-[(3S,4S)-4-{[(S)-1-(3,5-Bistrifluoromethylphenyl)ethyl]methylcarbamoyl}-3-(4-fluoro-2-methylphenyl)piperidin-1-ylmethyl]cyclohexyl}acetic acid To a mixture of cis-{4-[(3S,4S)-4-{[(S)-1-(3,5-bistrifluoromethylphenyl)ethyl]methylcarbamoyl}-3-(4-fluoro-2-methylphenyl)-piperidin-1-ylmethyl]cyclohexyl}acetic acid ethyl ester (0.035 g), tetrahydrofuran (1 mL), methanol (1 mL) and water (0.3 mL) was added lithium hydroxide monohydrate (0.011 g) at room temperature, and the mixture was stirred at the same temperature overnight. To the reaction mixture were added 1.0 mol/L hydrochloric acid (0.26 mL) and water, and the resulting mixture was extracted with ethyl acetate. The organic layer was dried over anhydrous magnesium sulfate. The solvent was concentrated under reduced pressure to give the title compound (0.020 g).

Example 14 trans-{4-[(3 S,4S)-4-{[(S)-1-(3,5-Bistrifluoromethylphenyl)ethyl]methylcarbamoyl}-3-(4-fluoro-2-methylphenyl)piperidin-1-ylmethyl]cyclohexyl}lacetic acid To a mixture of trans-{4-[(3S,4S)-4-{[(S)-1-(3,5-bistrifluoromethylphenyl)ethyl]methylcarbamoyl}-3-(4-fluoro-2-methylphenyl)-piperidin-1-ylmethyl]cyclohexyl}acetic acid ethyl ester (0.039 g), tetrahydrofuran (1 mL), methanol (1 mL) and water (0.3 mL) was added lithium hydroxide monohydrate (0.012 g) at room temperature, and the mixture was stirred at the same temperature overnight. To the reaction mixture were added 1.0 mol/L hydrochloric acid (0.29 mL) and water, and the resulting mixture was extracted with ethyl acetate. The organic layer was dried over anhydrous magnesium sulfate. The solvent was concentrated under reduced pressure to give the title compound (0.030 g).

Tables 1 to 6 show the chemical structures of the above compounds of Reference Examples 1 to 35, and the chemical structures and the physical properties of the above compounds of Examples 1 to 14. The abbreviations in these Tables: "Ref No.", "Ex No.", "Str.", "Physical data", "¹H-

NMR", and "CDCl$_3$" represent Reference Example number, Example number, chemical structure, physical property, proton nuclear magnetic resonance spectrum, and chloroform-d1, respectively. And, "MS" represent mass spectrometry and "ESI_APCI" indicates that it was measured by multi ionization method of electrospray ionization method-atmospheric pressure chemical ionization method, respectively.

TABLE 1

| Ref. No. | Str. |
|---|---|
| 1 | |
| 2 | |
| 3 | |
| 4 | |
| 5 | |
| 6 | |

TABLE 1-continued
| Ref. No. | Str. |
|---|---|
| 7 | 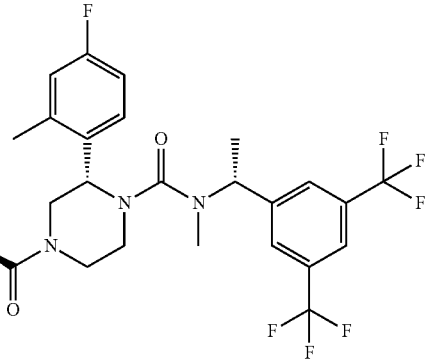 |
| 8 | 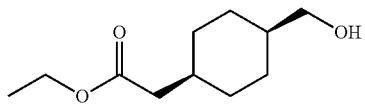 |
| 9 | 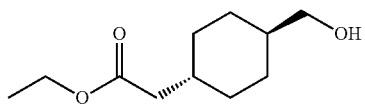 |
| 10 | 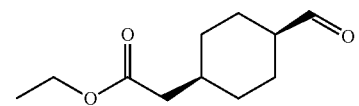 |
| 11 | 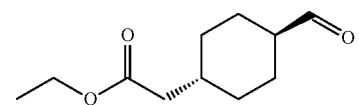 |
| 12 | 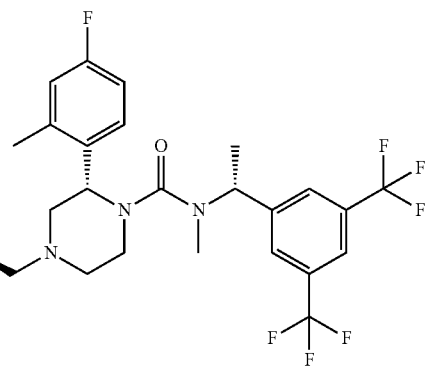 |
| 13 | 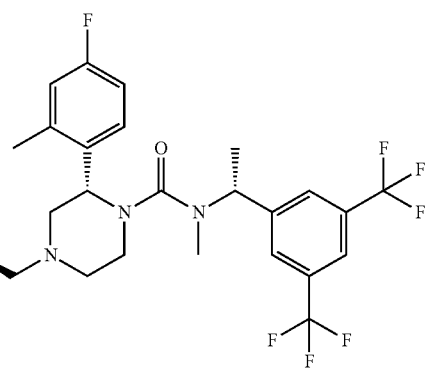 |

TABLE 1-continued

| Ref. No. | Str. |
|---|---|
| 14 | (structure: ethyl 4-[piperazine with (2-methyl-4-fluorophenyl) substituent, N-carboxamide linked to N-methyl-(1-(3,5-bis(trifluoromethyl)phenyl)ethyl)]cyclohexanecarboxylate) |

TABLE 2

| Ref. No. | Str. |
|---|---|
| 15 | methyl trans-4-(hydroxymethyl)cyclohexanecarboxylate |
| 16 | methyl cis-4-(hydroxymethyl)cyclohexanecarboxylate |
| 17 | methyl trans-4-formylcyclohexanecarboxylate |
| 18 | methyl cis-4-formylcyclohexanecarboxylate |
| 19 | methyl 4-{[4-((2S)-2-(4-fluoro-2-methylphenyl)piperazin-1-yl)carbonyl-N-methyl-N-[(1R)-1-(3,5-bis(trifluoromethyl)phenyl)ethyl]aminomethyl}cyclohexanecarboxylate |

TABLE 2-continued
| Ref. No. | Str. |
|---|---|
| 20 | 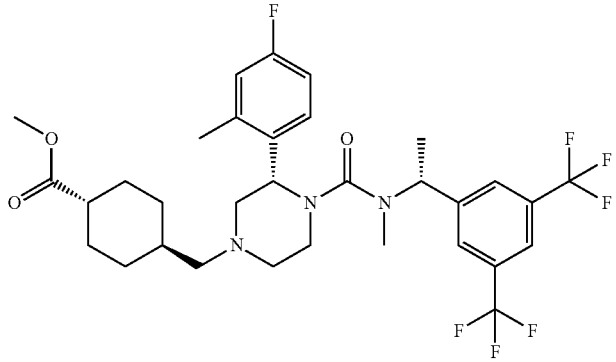 [SMILES: COC(=O)[C@H]1CC[C@H](CN2CCN(C(=O)N(C)[C@H](C)c3cc(C(F)(F)F)cc(C(F)(F)F)c3)[C@@H](c3ccc(F)cc3C)C2)CC1] |
| 21 | 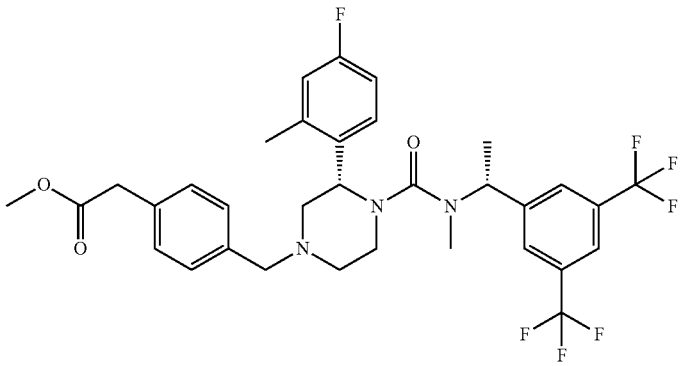 [SMILES: COC(=O)Cc1ccc(CN2CCN(C(=O)N(C)[C@H](C)c3cc(C(F)(F)F)cc(C(F)(F)F)c3)[C@@H](c3ccc(F)cc3C)C2)cc1] |
| 22 | 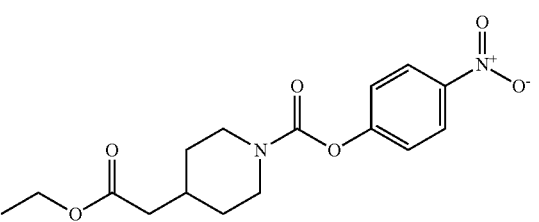 [SMILES: CCOC(=O)CC1CCN(C(=O)Oc2ccc([N+](=O)[O-])cc2)CC1] |
| 23 | 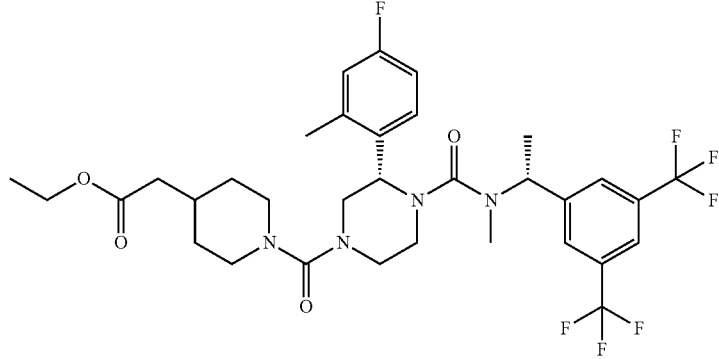 [SMILES: CCOC(=O)CC1CCN(C(=O)N2CCN(C(=O)N(C)[C@H](C)c3cc(C(F)(F)F)cc(C(F)(F)F)c3)[C@@H](c3ccc(F)cc3C)C2)CC1] |

TABLE 2-continued

| Ref. No. | Str. |
|---|---|
| 24 | (structure) |
| 25 | (structure) |
| 26 | (structure) |

TABLE 3

| Ref. No. | Str. |
|---|---|
| 27 | (structure) |
| 28 | (structure) |

TABLE 3-continued

| Ref. No. | Str. |
|---|---|
| 29 | |
| 30 | |
| 31 | |
| 32 | |
| 33 | |

TABLE 3-continued

| Ref. No. | Str. |
|---|---|
| 34 | (structure) |
| 35 | (structure) |

TABLE 4

| Ex. No. | Str. | Physical data |
|---|---|---|
| 1 | (structure) | MS (ESI_APCI, m/z): 632 (M + H)+ |
| 2 | (structure) | MS (ESI_APCI, m/z): 660 (M + H)+ |

TABLE 4-continued

| Ex. No. | Str. | Physical data |
|---|---|---|
| 3 | | MS (ESI_APCI, m/z): 660 (M + H)+ |
| 4 | | MS (ESI_APCI, m/z): 646 (M + H)+ |
| 5 | | MS (ESI_APCI, m/z): 646 (M + H)+ |

TABLE 5

| Ex. No. | Str. | Physical data |
|---|---|---|
| 6 | | MS (ESI_APCI, (m/z): 618 (M + H)+ |

TABLE 5-continued

| Ex. No. | Str. | Physical data |
|---|---|---|
| 7 | | MS (ESI_APCI, (m/z): 632 (M + H)+ |
| 8 | | MS (ESI_APCI, (m/z): 632 (M + H)+ |
| 9 | | 1H-NMR δ ppm (CDCl3): 1.48 (3H, d, J = 7.0 Hz), 2.20-3.80 (16H, m), 4.60-4.80 (1H, m), 5.40-5.55 (1H, m), 6.70-6.90 (2H, m), 7.15-7.45 (5H, m), 7.60 (2H, s), 7.77 (1H, s)<br>MS (ESI_APCI, m/z): 640 (M + H)+ |
| 10 | | MS (ESI_APCI, m/z): 661 (M + H)+ |

TABLE 6
| Ex. No. | Str. | Physical data |
|---|---|---|
| 11 | 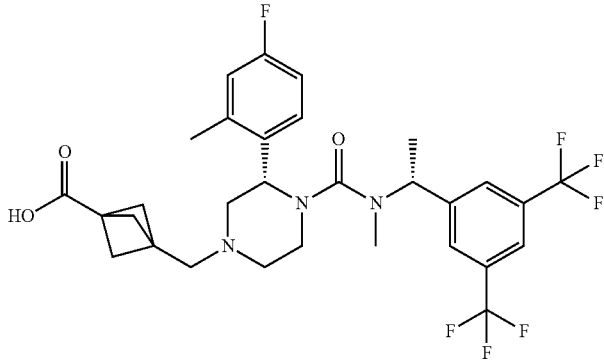 [SMILES: Cc1cc(F)ccc1[C@H]1CN(CC23CC(C(=O)O)(C2)C3)CCN1C(=O)N(C)[C@H](C)c1cc(C(F)(F)F)cc(C(F)(F)F)c1] | ¹H-NMR δ ppm (CDCl₃): 1.49 (3H, d, J = 6.8 Hz), 1.95-3.35 (20H, m), 4.60-4.80 (1H, m), 5.40-5.60 (1H, m), 6.70-6.95 (2H, m), 7.25-7.40 (1H, m), 7.61 (2H, s), 7.79 (1H, s)<br>MS (ESI_APCI, m/z): 616 (M + H)⁺ |
| 12 | 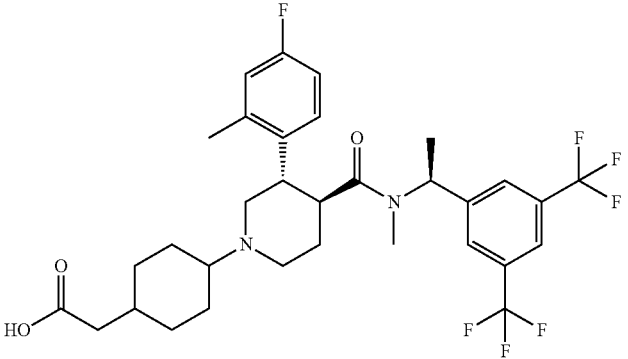 [SMILES: Cc1cc(F)ccc1[C@H]1CN(C2CCC(CC(=O)O)CC2)CC[C@@H]1C(=O)N(C)[C@@H](C)c1cc(C(F)(F)F)cc(C(F)(F)F)c1] | MS (ESI_APCI, m/z): 631 (M + H)⁺ |
| 13 | 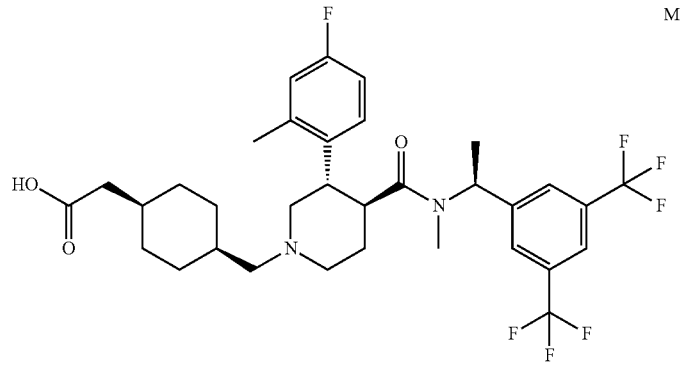 | MS (ESI_APCI, m/z): 645 (M + H)⁺ |
| 14 | 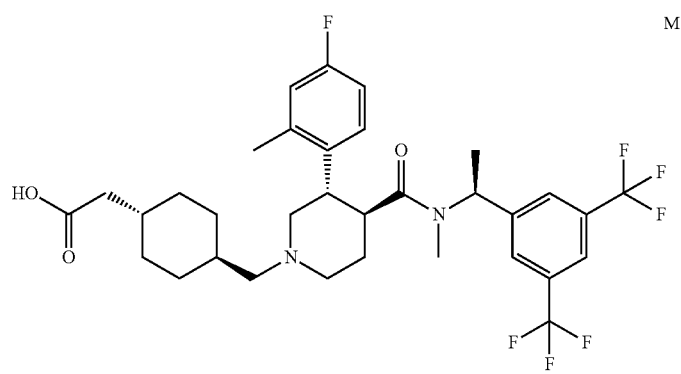 | MS (ESI_APCI, m/z): 645 (M + H)⁺ |

Test Example 1

Affinity for Human $NK_1$ Receptor (1) Preparation of Human $NK_1$ Receptor Expression Vector PCR was performed using human adult normal tissue-derived brain cDNA (BioChain) as the template, with the forward primer of SEQ ID NO:1 and the reverse primer of SEQ ID NO:2, using a PCR enzyme, PrimeSTAR Max DNA Polymerase or PrimeSTAR GXL DNA Polymerase® (Takara Bio). The amplified product was inserted into a plasmid (pCR-BluntII-TOPO®, Life Technologies) using Zero Blunt PCR Cloning Kit®, Life Technologies). By a general method, Escherichia coli One Shot TOP10 competent cells, Life Technologies) was transformed by the plasmid into which the amplified product had been inserted. The Escherichia coli cells were cultured on an LB agar medium containing 50 µg/mL kanamycin for a day. After the culture, a colony was selected and cultured in an LB medium containing 50 µg/mL kanamycin. After the culture, the plasmid was purified using Quantum Prep Plasmid Miniprep Kit (Bio-Rad). The plasmid was double digested for about 2 hours using restriction enzymes, XhoI and HindIII (New England Biolabs). Then, electrophoresis using 1% agarose gel was performed, and the fragment that was cleaved was collected and purified using TaKaRa RICOCHIP (Takara Bio). Separately, a plasmid was also purified from Escherichia coli that had been transformed by a vector (pcDNA3.1 (-)®, Life Technologies), and the plasmid was double digested for about 2 hours using restriction enzymes, XhoI and HindIII (New England Biolabs). Then, electrophoresis using 1% agarose gel was performed, and the vector that was cleaved was collected and purified using TaKaRa RICO-CHIP (Takara Bio). The fragment cut out of pCR-Blunt-II and the pcDNA3.1(-) vector treated with the restriction enzymes were ligated using DNA Ligation Kit <Mighty Mix> (Takara Bio). By a general method, Escherichia coli (One Shot TOP10 competent cells, Life Technologies) was transformed by the plasmid obtained by the ligation. The Escherichia coli cells were cultured on an LB agar medium containing 50 µg/mL ampicillin for a day. After the culture, a colony was selected and cultured in an LB medium containing 50 µg/mL ampicillin, and then the plasmid was purified using Quantum Prep Plasmid Miniprep Kit (Bio-Rad). The protein-encoding nucleotide sequence (SEQ ID NO: 3) of the obtained plasmid was completely identical to the nucleotide sequence (NM_001058.3) of human tachykinin receptor 1 (TACR1, NK1R) registered on a known database (NCBI). Therefore, it was confirmed that the cloned gene sequence was the nucleotide sequence of human $NK_1$ receptor and that the amino acid sequence which would be translated was human $NK_1$ receptor. The pcDNA3.1(-)® into which the nucleotide sequence of SEQ ID NO: 3 was inserted was used as the human $NK_1$ receptor expression plasmid.

(2) Preparation of Human $NK_1$ Receptor-Expressing Cells (2-1) Culture of 293T Cells Using a liquid D-MEM (Dulbeccos Modified Eagle Medium) medium (low glucose, containing L-glutamine, Wako Pure Chemical Industries) supplemented with an antibiotic penicillin-streptomycin solution (Life Technologies, final penicillin concentration of 100 U/mL and final streptomycin concentration of 100 µg/mL) and fetal bovine serum (final concentration of 10%), 293T cells (RIKEN) were cultured in an incubator under the condition of 5% $CO_2$ gas at 37° C.

(2-2) Subculture of 293T Cells

Almost confluent cells were washed with PBS (Phosphate Buffered Saline, Wako Pure Chemical Industries), detached using 0.05% trypsin-EDTA (Life Technologies) and suspended in the liquid medium. The cell suspension was diluted with the above liquid medium in such a manner that the spread ratio became 1:10, and then the cells were cultured.

(2-3) Preparation for Human $NK_1$ Receptor-Expressing Cells

Confluent cells were washed with PBS, detached using 0.05% trypsin-EDTA (Life Technologies) and suspended in a liquid D-MEM medium (low glucose, containing L-glutamine, Wako Pure Chemical Industries) supplemented with fetal bovine serum (final concentration of 10%). The cell suspension was diluted with the liquid medium, and the cells were seeded into the wells of a poly-D-lysine-coated 96-well microplate (BD Biocoat®, Nippon Becton Dickinson) at a density of $5 \times 10^4$ cells/well and a liquid medium volume of 100 µL/well. After seeding, the cells were cultured in an incubator under the condition of 5% $CO_2$ gas at 37° C. for about 4 to 5 hours, and the cells to be transfected with the human $NK_1$ receptor expression plasmid were thus prepared.

(2-4) Transfection of Human $NK_1$ Receptor Expression Plasmid into 293T Cells

For the transfection of the human $NK_1$ receptor expression plasmid, Lipofectamine 2000® (Life Technologies) was used. The human $NK_1$ receptor expression plasmid was diluted with Opti-MEM® I Reduced-Serum Medium (Life Technologies) to a concentration resulting in 0.2 µg/25 µL/well. At the same time, Lipofectamine 2000® (Life Technologies) was diluted with Opti-MEM® I Reduced-Serum Medium (Life Technologies) to a concentration resulting in 0.4 µL/25 µL/well and incubated at room temperature for 5 minutes. After 5 minutes, to form a complex of human $NK_1$ receptor expression plasmid/Lipofectamine 2000, the diluted human $NK_1$ receptor expression plasmid and the diluted Lipofectamine 2000 were mixed and incubated at room temperature for 20 to 25 minutes. After the incubation, 50 µL/well of the complex solution was added to the cells to be transfected with the human $NK_1$ receptor expression plasmid, and the cells were cultured in an incubator under the condition of 5% $CO_2$ gas at 37° C. for about 48 hours. The cells that were cultured for 48 hours were used for the assays as the human $NK_1$ receptor-expressing cells.

(3) Measurement of Binding Affinity to Human $NK_1$ Receptor (3-1) Preparation of Membrane Fraction from Human $NK_1$ Receptor-Expressing Cells Human $NK_1$ receptor-expressing cells were prepared in a 175 $cm^2$ culture flask (Nippon Becton Dickinson). The formation of a complex of the human $NK_1$ receptor expression plasmid and Lipofectamine 2000 was performed by calculating the culture area ratio and increasing the scale of the method described in the above 2-4 by the ratio. The human $NK_1$ receptor-expressing cells were collected in a buffer solution for the membrane fraction preparation (50 mM Tris (Wako Pure Chemical), 120 mM sodium chloride (Wako Pure Chemical Industries), 5 mM potassium chloride (Wako Pure Chemical Industries), 1 mM ethylenediaminetetraacetic acid (Sigma), 0.002 mg/mL chymostatin (Peptide Institute), 0.04 mg/bacitracin (Wako Pure Chemical Industries), 0.005 mg/mL phosphoramidon (Peptide Institute) and 0.5 mM phenylmethylsulfonyl fluoride (Wako Pure Chemical Industries), pH7.4) and centrifuged at 1,880 g for 10 minutes, and the cell sediment was suspended in the buffer solution for the membrane fraction preparation. After freezing and thawing the cells once, the cells were homogenized using a Dounce-type homogenizer (cooled on ice, 1000 rpm, 20 times). The homogenized cell suspension was centrifuged at 20,000 rpm for 10 minutes, and the supernatant was removed to obtain cell sediment. The cell sediment was suspended again in the buffer solution for the membrane fraction preparation and homogenized using a Dounce-type homogenizer (cooled on ice, 1000 rpm, 30 times). The cell suspension was centrifuged at 20,000 rpm for 10 minutes, and the supernatant was removed to obtain cell sediment. The same homogenization and centrifugation were repeated again, and final cell sediment was obtained. The final cell sediment was suspended in a buffer solution for the receptor binding test (50 mM Tris (Wako Pure Chemical Industries), 3 mM manganese chloride (Wako Pure Chemical Industries), 0.002 mg/mL chymostatin (Peptide Institute), 0.04 mg/bacitracin (Wako Pure Chemical Industries) and 0.02% bovine serum albumin (Sigma), pH 7.4), and the protein concentration was measured using BCA Protein Assay Kit (Pierce).

(3-2) Receptor Binding Test

The buffer solution for the receptor binding test was dispensed to the wells of a 96-well assay plate (Greiner) at 22.5 μL/well. DMSO solutions of a test compound, which were prepared at an 80-time higher concentration using 100% dimethyl sulfoxide (DMSO), were added to the wells at 2.5 μL/well (final concentrations of 1 nM to 100 nM), and the solutions were mixed. As a radiolabeled ligand, $^{125}$I-substance P (Substance P, [$^{125}$I]Tyr$^8$-, PerkinElmer) was used. $^{125}$I-substance P was diluted with the buffer solution for the receptor binding test to a concentration resulting in 125 pmol/25 μL/well and added to the 96-well assay plate, and the solutions were mixed. The membrane fraction prepared from the human $NK_1$ receptor-expressing cells was diluted with the buffer solution for the receptor binding test to a concentration resulting in 8 to 10 μg/well, suspended until the suspension became in such a homogenous state that the suspension could flow through a 27G injection needle smoothly and then added to the 96-well assay plate at 150 μL/well. Then, the plate was incubated at room temperature for 60 minutes while shaking the plate. The reaction solutions were suction-filtered through a multiscreen 96-well filter plate (Millipore) which had been pre-treated with 0.3% polyethyleneimine, and the reaction was terminated by washing with a washing solution (50 mM Tris and 0.02% bovine serum albumin, pH four times. The bottom of the microplate was dried at 60° C., and then 100 μL/well of MicroScint 20 (PerkinElmer) was dispensed to the wells. The top of the plate was sealed with TopSeal A (PerkinElmer), and the plate was shaken for 5 to 10 minutes. Then, the radioactivities were measured with TopCount NXT® (PerkinElmer). The radioactivity of each well was calculated by subtracting the radioactivity of the well to which 10 μM aprepitant was added (non-specific binding). The binding rate (%) of $^{125}$I-substance P=(the radioactivity of the group to which the test compound was added)/(the radioactivity of the group to which the vehicle was added)×100 was calculated, and then the binding rate (%) was plotted against the concentration of the test compound, and inverse logarithm of the concentration required for 50% inhibition, pIC50, was calculated by using Microsoft Excel® (Microsoft Corporation). These results were shown in Table 7. In the table, Ex. No. means the Example number, and $pIC_{50}$ means inverse logarithm of the concentration required for 50% inhibition.

(4) Results

TABLE 7

| Ex. No. | $pIC_{50}$ |
| --- | --- |
| 1 | 8.65 |
| 2 | 8.86 |
| 3 | 8.85 |

TABLE 7-continued

| Ex. No. | $pIC_{50}$ |
| --- | --- |
| 4 | 9.07 |
| 5 | 9.07 |
| 6 | 8.77 |
| 7 | 8.69 |
| 8 | 8.73 |
| 9 | 8.81 |
| 10 | 8.93 |
| 11 | 8.72 |
| 12 | 9.55 |
| 13 | 9.19 |
| 14 | 8.87 |

As shown in Table 7, it was demonstrated that the compounds of the present invention exhibit a high binding affinity for human $NK_1$ receptor.

Test Example 2

Inhibitory Effect on Human $NK_1$ Receptor (1) Preparation of Human $NK_1$ Receptor-Expressing Cells Human $NK_1$ receptor-expressing cells were prepared by the same methods as those described in 2-3 and 2-4 of Test Example 1.

(2) Study on Inhibitory Effect on Increase in Intracellular Calcium Concentration The human $NK_1$ receptor-expressing cells were washed with 300 μL/well of a washing solution (20 mM HEPES/Hanks Balanced Salt Solution (HBSS) pH7.3). A fluorescent calcium indicator (Fluo-4 Direct Calcium Assay Kit, Life Technologies, containing 0.42 mM probenecid and 0.1% bovine serum albumin, prepared according to the protocol of the product) was added to the wells at 150 μL/well, and the plate was incubated at 37° C. for 30 minutes in an incubator. Then, DMSO solutions of a test compound, which were prepared at an 80-time higher concentration using 100% dimethyl sulfoxide (DMSO), were added to the wells at 2.5 μL/well (final concentrations of 0.1, 1 and 10 μM), and the solutions were mixed. Then, the plate was further incubated at 37° C. for 30 minutes in an incubator. After 30 minutes, the intracellular calcium concentrations were measured immediately.

The intracellular calcium concentrations were each measured as a fluorescent signal using FDSS® 7000 (Hamamatsu Photonics). A substance P (Peptide Institute, Inc.) solution which was prepared at 0.4 μM or 4 μM using an assay buffer (20 mM HEPES/Hanks Balanced Salt Solution (HBSS) pH 7.3 containing 0.1% bovine serum albumin) was added automatically to each well at 50 μL/well (final concentration of 0.1 or 1 μM) 10 seconds after starting reading, and the fluorescent signal was measured up to 120 seconds.

The intracellular calcium concentration (%) of the cells to which a test compound was added was calculated by the equation below, where the fluorescent signal of the group to which the vehicle (DMSO) was added was regarded as 100%, and the fluorescent signal before the addition of substance P was regarded as 0%.

Intracellular calcium concentration (%)=(Fluorescent signal of test compound addition group)/(Fluorescent signal of vehicle addition group)×100

The intracellular calcium concentration (%) calculated was regarded as the remaining agonist activity of substance P (Substance P-Response Remaining: SPRR). These results were shown in Table 8. In the table, Ex. No. means the Example number. SPRR (%) means the value obtained when the concentration of substance P was 0.1 µM and the concentration of the compound was 1 µM.

(3) Results

TABLE 8

| Ex. No. | SPRR (%) |
|---|---|
| 1 | 15 |
| 2 | 25 |
| 3 | 50 |
| 4 | 2.1 |
| 5 | 8.9 |
| 6 | 14 |
| 7 | 6.6 |
| 8 | 14 |
| 9 | 38 |
| 10 | 30 |
| 11 | 24 |
| 12 | 4.9 |
| 13 | 4.1 |
| 14 | 14 |

As shown in Table 8, it was demonstrated that the compounds of the present invention exhibit a human $NK_1$ receptor antagonist activity.

Test Example 3

Inhibitory Effect on CYP3A4

The dimethyl sulfoxide (DMSO) solution of the test compound with a concentration 1000 times higher than the evaluation concentration was prepared, and a reaction solution was prepared by diluting the solution. Enzyme reaction was performed by incubating in a potassium phosphate buffer solution (pH 7.4) containing 1 µM to 10 µM test compound, 3.2 mM magnesium chloride, 0.2 pmol human CYP3A4 (BD Biosciences), 0.5 mM reduced nicotinamide adenine dinucleotide phosphate (NADPH) and 3 µM Luciferin-IPA (Promega) at 37° C. for 10 minutes. The volume of the reaction solution was 50 µL/well. The 30-minutes pre-incubation group was incubated at 37° C. for 30 minutes before adding the substrate, the Luciferin-IPA solution (12.5 µL/well). At the end of the enzyme reaction, 50 µL/well of a Luciferin detection reagent (Promega) was added to the wells, and the plate was left at room temperature for 20 minutes. Then, the emission intensities were measured with Infinite M1000 (TECAN), and the enzyme activities (%) relative to the value of the group to which the test compound was not added. As a comparative example, aprepitant, which is an $NK_1$ receptor antagonist, was tested in the same manner.

Test was measured by the above test method, and the results are shown in Table 9 when the concentration of the test compound was 10 µM. In the table, Ex. No. means the Example number, and Pre-incubation (30 min) (%) means the enzyme activities (%) of the 30-minutes pre-incubation groups using the test compounds.

TABLE 9

| Ex. No. | Preincubation (30 min) (%) |
|---|---|
| 4 | 18 |
| 5 | 21 |
| 13 | 18 |
| 14 | 15 |
| Aprepitant | 1.3 |

As shown in Table 9, it was demonstrated that the CYP3A4-inhibitory activities of the compounds of the present invention are reduced as compared to that of aprepitant. Therefore, it is expected that the compounds of the present invention have fewer drug-drug interactions based on the inhibitory effect on CYP3A4 than aprepitant.

Test Example 4

Effect on Foot-tapping (1) Effect on Foot-tapping

The test compound solution was prepared by dissolving the test compound in a vehicle (a mixture of 50% N,N-dimethylacetamide (Wako Pure Chemical Industries), 30% propylene glycol (Wako Pure Chemical Industries), 4% 2-hydroxypropyl-β-cyclodextrin (Wako Pure Chemical Industries) and 16% distilled water).

A male gerbil (Japan SLC) was anesthetized with isoflurane, and 0.3 mg/kg of a test compound was administered from the jugular vein. After 4 hours, GR73632 (5 pmol/5 µL saline), which is an $NK_1$ receptor agonist, was administered into the cerebral ventricle at the part 1 mm lateral to and 4.5 mm below the bregma in the head, under anesthesia with isoflurane. After the administration, the gerbil was moved to an observation cage, and the foot-tapping period during 30 minutes after the recovery of the righting reflex was measured. As a comparative example, aprepitant, which is an $NK_1$ receptor antagonist, was tested in the same manner. The foot-tapping inhibition rate (%) of each test compound was calculated by the following equation.

Foot-tapping inhibition rate (%)={1−(Foot-tapping period when test compound was administered)/(Foot-tapping period when solvent was administered)}×100

(2) Measurement of Drug Concentrations

After foot-tapping was finished, laparotomy was performed immediately under anesthesia with ether, and a blood sample was taken from the abdominal vena cava. At the same time, the brain was extracted. Through a quantitative analysis using liquid chromatography-mass spectrometry (LC/MS), the concentrations of the test compound in the plasma and the brain were measured.

(3) Results

The effects on foot-tapping were measured by the above test method, and the results are shown in Table 10. In the table, Ex. No. means the Example number. Inhibition (%) means the foot-tapping inhibition rate, and Conc. (nM) means the drug concentration in the brain.

TABLE 10

| Ex. No. | Inhibition(%) | Conc. (nM) |
|---|---|---|
| 4 | 100 | 162 |
| 5 | 100 | 181 |

As shown in Table 10, the compounds of the present invention were penetrated into the central nervous system and exhibited an excellent $NK_1$ receptor antagonist activity also in vivo.

INDUSTRIAL APPLICABILITY

The compounds of the present invention or pharmaceutically acceptable salts thereof have an excellent $NK_1$ receptor antagonist activity, and thus are also useful as an agent for the prevention or treatment of cancer-chemotherapy-induced nausea and vomiting.

Sequence Listing Free Text

<Sequence Listing 1>

SEQ ID NO: 1 is the sequence of forward primer which was used for DNA amplification of SEQ ID NO: 3.

<Sequence Listing 2>

SEQ ID NO: 2 is the sequence of reverse primer which was used for DNA amplification of SEQ ID NO: 3.

The invention claimed is:
1. A compound represented by the formula (I):

[Chem. 1]

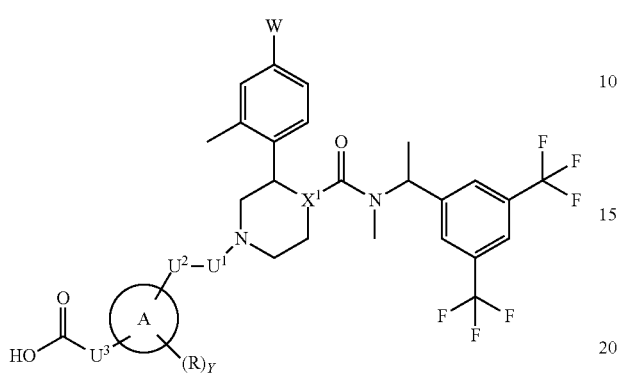

(I)

wherein
W is a hydrogen atom or a fluorine atom;
Ring A is a group selected from the group consisting of the following (a) to (d):

[Chem. 2]

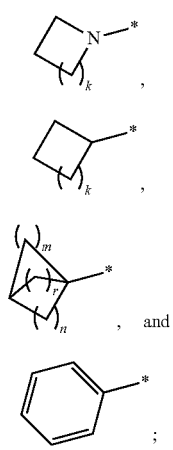

wherein
bond with * is a bonding site to the $U^2$;
k represents an integer number 1 to 5;
r is 1 or 2;
m and n are independently 1, 2 or 3;
$X^1$ is N;
R is a methyl, hydroxy or a halogen atom;
Y is 0, 1 or 2;
when Y is 2, two R are optionally different from each other;
$U^1$, $U^2$ and $U^3$ are each independently a single bond, carbonyl or a methylene which may have any group selected from substituent group α;
when ring A is a group represented by the above (a), either one of $U^1$ or $U^2$ is carbonyl; substituent group α is a group consisting of a halogen atom, hydroxy, a $C_{1-6}$ alkyl and a $C_{1-6}$ alkoxy;
or a pharmaceutically acceptable salt thereof.

2. The compound according to claim 1, or a pharmaceutically acceptable salt thereof, wherein W is a fluorine atom.
3. The compound represented by the formula (Ia) according to claim 2:

[Chem. 3]

(Ia)

wherein
ring B is a group represented by the following formula:

[Chem. 4]

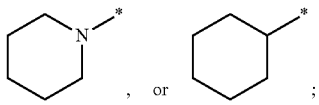

wherein
bond with * is a bonding site to the $U^2$;
$U^1$, $U^2$ and $U^3$ are each independently a single bond, carbonyl or a methylene which may have any group selected from substituent group α;
or a pharmaceutically acceptable salt thereof.

4. The compound represented by the formula (Ib) according to claim 3:

[Chem. 5]

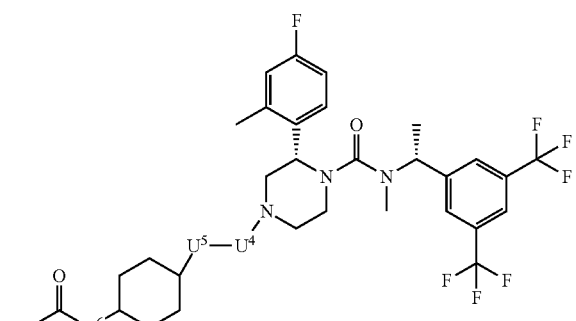

(Ib)

wherein
$U^4$, $U^5$ and $U^6$ are each independently a single bond or a methylene which may have any substituent selected from substituent group α;
substituent group α is a group consisting of a halogen atom, hydroxy, a $C_{1-6}$ alkyl and a $C_{1-6}$ alkoxy;
or a pharmaceutically acceptable salt thereof.

5. The compound represented by the formula (Ic) according to claim 4:

[Chem. 6]

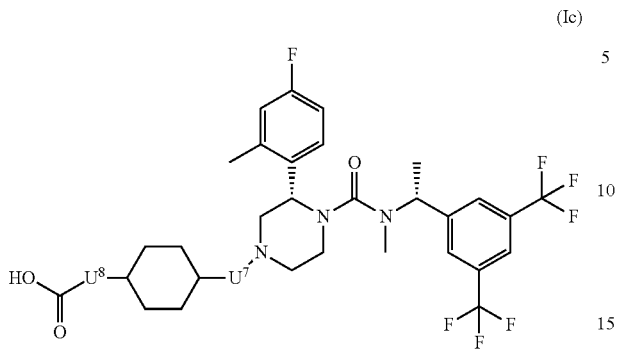

(Ic)

wherein
U⁷ and U⁸ are each independently a single bond or a methylene which may have any substituent selected from substituent group β;
substituent group β is a group consisting of a fluorine atom and methyl;
or a pharmaceutically acceptable salt thereof.

6. The compound represented by the formula (Id) according to claim 5:

[Chem. 7]

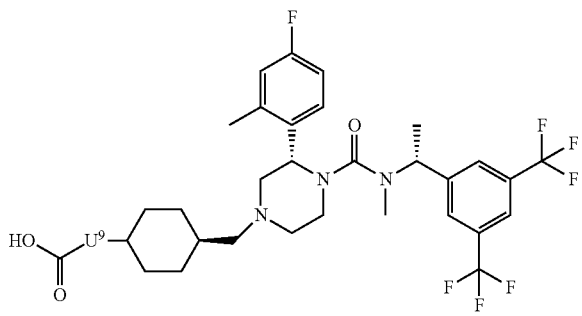

(Id)

wherein
U⁹ is a single bond or methylene;
or a pharmaceutically acceptable salt thereof.

7. The compound represented by the formula (Ie):

[Chem. 8]

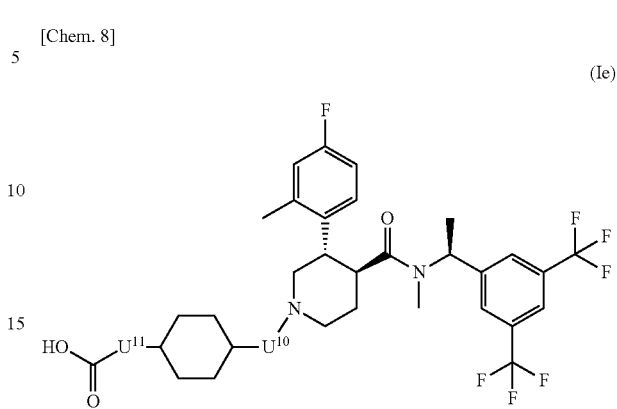

(Ie)

wherein
U¹⁰ and U¹¹ are each independently a single bond or methylene;
or a pharmaceutically acceptable salt thereof.

8. A pharmaceutical composition comprising the compound according to claim 1 or a pharmaceutically acceptable salt thereof.

9. A method of preventing or treating cancer-chemotherapy-induced nausea and vomiting, comprising administering the pharmaceutical composition according to claim 8 to a subject in need thereof.

10. A pharmaceutical composition comprising the compound according to claim 7 or a pharmaceutically acceptable salt thereof.

11. A method of preventing or treating cancer-chemotherapy-induced nausea and vomiting, comprising administering the pharmaceutical composition according to claim 10 to a subject in need thereof.

\* \* \* \* \*

UNITED STATES PATENT AND TRADEMARK OFFICE
CERTIFICATE OF CORRECTION

PATENT NO.         : 10,399,949 B2
APPLICATION NO.    : 15/781925
DATED              : September 3, 2019
INVENTOR(S)        : Takashi Miyagi, Masahiro Kobayashi and Toshihiro Nishimura It is certified that error appears in the above-identified patent and that said Letters Patent is hereby corrected as shown below:

In the Specification

At Column 7, starting at Line 5:
Please delete:
"Scheme 2
[Chem. 10]

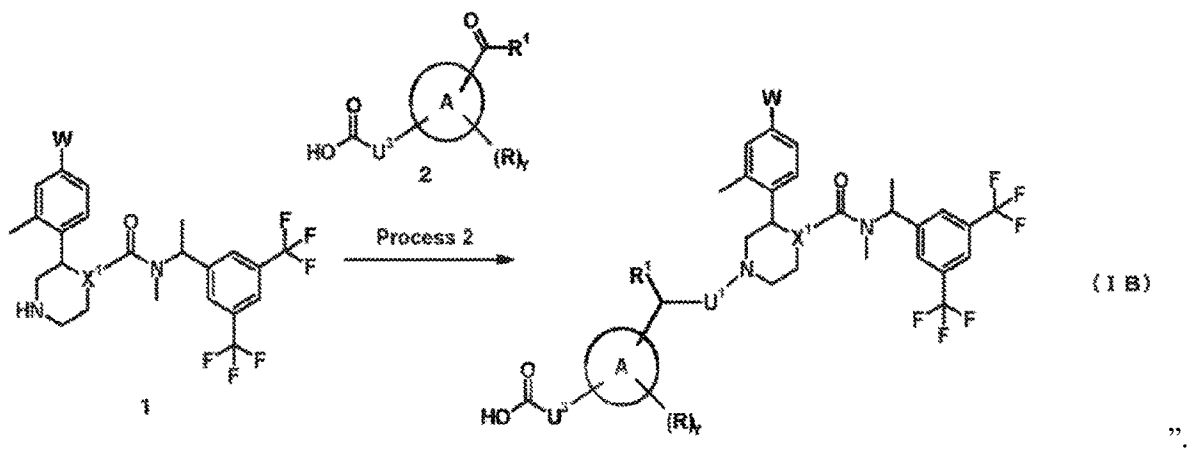

At Column 7, after the paragraph reading "A compound represented by the formula (IA) can be prepared, for example, by a method described in Process 1 of Scheme 1":
Please insert:
-- Scheme 1
[Chem. 9]

Signed and Sealed this
Third Day of March, 2020

Andrei Iancu
*Director of the United States Patent and Trademark Office*

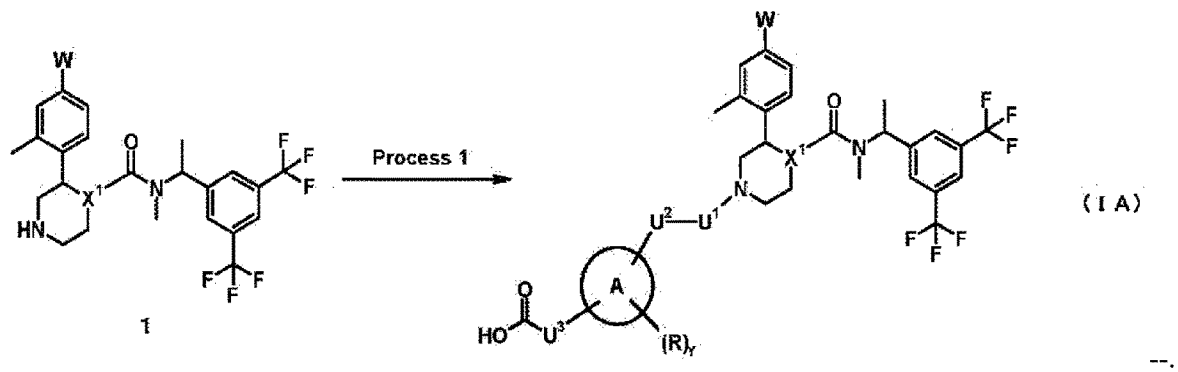
At Column 8, starting at Line 1:
Please delete:
"Scheme 1
[Chem. 9]
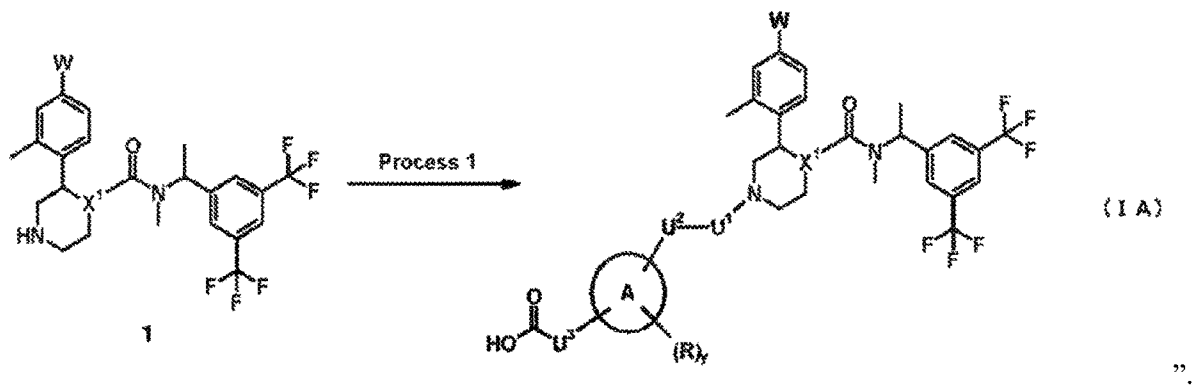
".
At Column 8, after the paragraph reading "A compound represented by the formula (IB) can be prepared, for example, by a method described in Process 2 of Scheme 2":
Please insert:
-- Scheme 2
[Chem. 10]
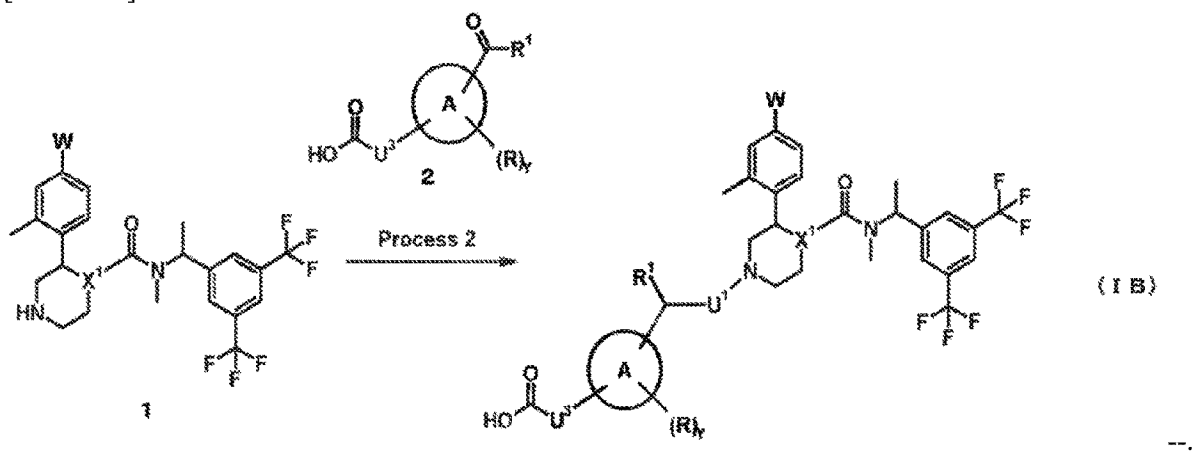
--.

At Column 8, Line 56:
Please change "formula (TB)" to be -- "formula (IB)" --.

At Column 8, Line 66:
Please change "Compound (TB)" to be -- "Compound (IB)" --.